US009913924B2

(12) United States Patent
Adair et al.

(10) Patent No.: US 9,913,924 B2
(45) Date of Patent: Mar. 13, 2018

(54) DISPENSING DEVICE

(71) Applicant: S.C. JOHNSON & SON, INC., Racine, WI (US)

(72) Inventors: Joel E. Adair, Racine, WI (US); Brian T. Davis, Burlington, WI (US); Gregory A. Falduto, Grayslake, IL (US); Michelle Dekea Fason, Kenosha, WI (US); Kamran Faterioun, New Berlin, WI (US); Donald J. Schumacher, Racine, WI (US); Paulina Carlos Trevino, Chicago, IL (US); Katlyn Ross, McFarland, WI (US); Shawn Smith, Madison, WI (US); Evan A. Sparks, Madison, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 66 days.

(21) Appl. No.: 15/164,580

(22) Filed: May 25, 2016

(65) Prior Publication Data

US 2017/0340765 A1 Nov. 30, 2017

(51) Int. Cl.
*A61L 9/12* (2006.01)
*B01F 3/04* (2006.01)

(52) U.S. Cl.
CPC ............ *A61L 9/12* (2013.01); *B01F 3/04085* (2013.01); *A61L 2209/133* (2013.01)

(58) Field of Classification Search
CPC ........... A61L 9/12; B01F 3/04; B01F 3/04085

USPC .............................. 261/100, DIG. 88; 239/53
See application file for complete search history.

(56) References Cited

U.S. PATENT DOCUMENTS

| 2,579,715 A | 12/1951 | Saeks et al. |
| 3,378,333 A | 4/1968 | Brite |
| 3,424,960 A | 1/1969 | Ross |
| 3,522,935 A | 8/1970 | Lewis |
| 4,016,439 A | 4/1977 | Sheridan |
| 5,029,408 A | 7/1991 | Smith |
| 5,104,626 A | 4/1992 | Yang |
| 5,216,919 A | 9/1993 | King |
| 5,480,591 A | 1/1996 | Lagneaux et al. |
| 5,611,165 A | 3/1997 | Blaha |
| 5,695,692 A | 12/1997 | Kennedy |
| 5,822,277 A | 10/1998 | Van Amersfoot et al. |
| 5,961,043 A | 10/1999 | Samuelson et al. |
| 6,080,367 A | 6/2000 | Lin |
| 6,143,313 A | 11/2000 | Ito et al. |
| 6,149,038 A | 11/2000 | Tsai |

(Continued)

FOREIGN PATENT DOCUMENTS

| CN | 101443052 B | 5/2014 |
| DE | 19631424 A1 | 2/1998 |

(Continued)

OTHER PUBLICATIONS

International Search Report and Written Opinion related PCT Application PCT/US2017/032335 dated Aug. 17, 2017 (4 pages).

*Primary Examiner* — Robert A Hopkins

(57) ABSTRACT

A dispensing device for release of a volatile material includes a base, a drive arm coupled to a pendulum based drive mechanism, and a refill coupled to the drive arm. The refill includes a support base, at least one flange, a substrate coupled with the at least one flange, and a use-up cue.

20 Claims, 23 Drawing Sheets

(56) References Cited

U.S. PATENT DOCUMENTS

| | | |
|---|---|---|
| 6,179,275 B1 | 1/2001 | Lagneaux et al. |
| 6,289,889 B1 | 9/2001 | Bell et al. |
| 6,425,530 B1 | 7/2002 | Coakley |
| 6,548,015 B1 | 4/2003 | Stubbs et al. |
| 6,582,714 B1 | 6/2003 | Emmrich et al. |
| 6,632,405 B2 | 10/2003 | Lua |
| 6,767,521 B1 | 7/2004 | Vogt et al. |
| 6,871,794 B2 | 3/2005 | McEwen |
| 6,901,609 B2 | 6/2005 | Hill |
| 6,944,889 B2 | 9/2005 | Hill |
| 7,007,861 B2 | 3/2006 | Ketcha et al. |
| 7,081,211 B2 | 7/2006 | Li et al. |
| 7,152,809 B2 | 12/2006 | Ketcha et al. |
| 7,168,630 B1 | 1/2007 | Ketcha et al. |
| 7,235,187 B2 | 6/2007 | Li et al. |
| 7,452,503 B2 | 11/2008 | Hart et al. |
| 7,523,577 B2 | 4/2009 | Majerowski |
| 7,530,503 B2 | 5/2009 | Caserta |
| 7,548,684 B2 | 6/2009 | Berrido |
| 7,665,238 B2 | 2/2010 | Majerowski |
| 7,718,119 B2 | 5/2010 | Tajima et al. |
| 7,771,665 B2 | 8/2010 | Pohl et al. |
| 7,793,861 B2 | 9/2010 | Bankers et al. |
| 8,043,569 B2 * | 10/2011 | Tranzeat ............. A01M 1/2033 422/124 |
| 8,286,894 B2 | 10/2012 | Perez et al. |
| 8,369,694 B2 | 2/2013 | Pitz et al. |
| 8,372,349 B1 | 2/2013 | Shotey et al. |
| 8,480,248 B2 | 7/2013 | Demarest et al. |
| 8,496,881 B2 | 7/2013 | Pohl et al. |
| 8,882,998 B2 | 11/2014 | Tranzeat et al. |
| 2002/0197188 A1 | 12/2002 | Lua |
| 2004/0050950 A1 | 3/2004 | Brown |
| 2004/0250962 A1 | 12/2004 | Hart |
| 2004/0261790 A1 | 12/2004 | Joshi et al. |
| 2005/0089502 A1 | 4/2005 | Schansberg et al. |
| 2006/0110281 A1 | 5/2006 | Smith |
| 2006/0225728 A1 | 10/2006 | Atkinson |
| 2007/0140923 A1 | 6/2007 | Wiegand |
| 2007/0257016 A1 | 11/2007 | Jin et al. |
| 2008/0155886 A1 | 7/2008 | Okuda |
| 2009/0185951 A1 | 7/2009 | Litten-Brown et al. |
| 2010/0140372 A1 | 6/2010 | Patrick |
| 2010/0187324 A1 | 7/2010 | Feygin et al. |
| 2010/0230509 A1 | 9/2010 | Beal |
| 2011/0262377 A1 | 10/2011 | McKay et al. |
| 2011/0290908 A1 | 12/2011 | Transeat et al. |
| 2011/0318296 A1 | 12/2011 | Braun et al. |
| 2012/0048964 A1 | 3/2012 | Willert |
| 2012/0091221 A1 | 4/2012 | Levake et al. |
| 2012/0328689 A1 | 12/2012 | Flynn et al. |
| 2014/0027530 A1 | 2/2014 | Cao et al. |
| 2014/0239079 A1 | 8/2014 | Wolf |
| 2015/0021408 A1 | 1/2015 | Matthews |
| 2015/0297774 A1 | 10/2015 | Thompson et al. |
| 2015/0359227 A1 | 12/2015 | Widder et al. |

FOREIGN PATENT DOCUMENTS

| | | |
|---|---|---|
| EP | 239802 A2 | 10/1987 |
| FR | 2430238 A1 | 2/1980 |
| FR | 3001864 A1 | 8/2014 |
| GB | 1516845 A | 7/1978 |
| JP | S61152601 A | 7/1986 |
| JP | 4922578 B2 | 4/2012 |
| JP | 2014-036677 A | 2/2014 |
| JP | 2014-073089 A | 4/2014 |
| JP | 2014-083023 A | 5/2014 |
| WO | 1999048469 A1 | 9/1999 |
| WO | 1999048539 A1 | 9/1999 |
| WO | 00/35497 A2 | 6/2000 |
| WO | 01/93674 A2 | 12/2001 |
| WO | 2006088139 A1 | 8/2006 |
| WO | 2006-128316 A1 | 12/2006 |
| WO | 2010070576 A1 | 6/2010 |
| WO | 2014018594 A1 | 1/2014 |
| WO | 2014029993 A1 | 2/2014 |
| WO | 2015006969 A1 | 1/2015 |
| WO | 2015008083 A1 | 1/2015 |
| WO | 2015161266 A1 | 10/2015 |
| WO | 2015164849 A1 | 10/2015 |
| WO | 2016092137 A1 | 6/2016 |

* cited by examiner

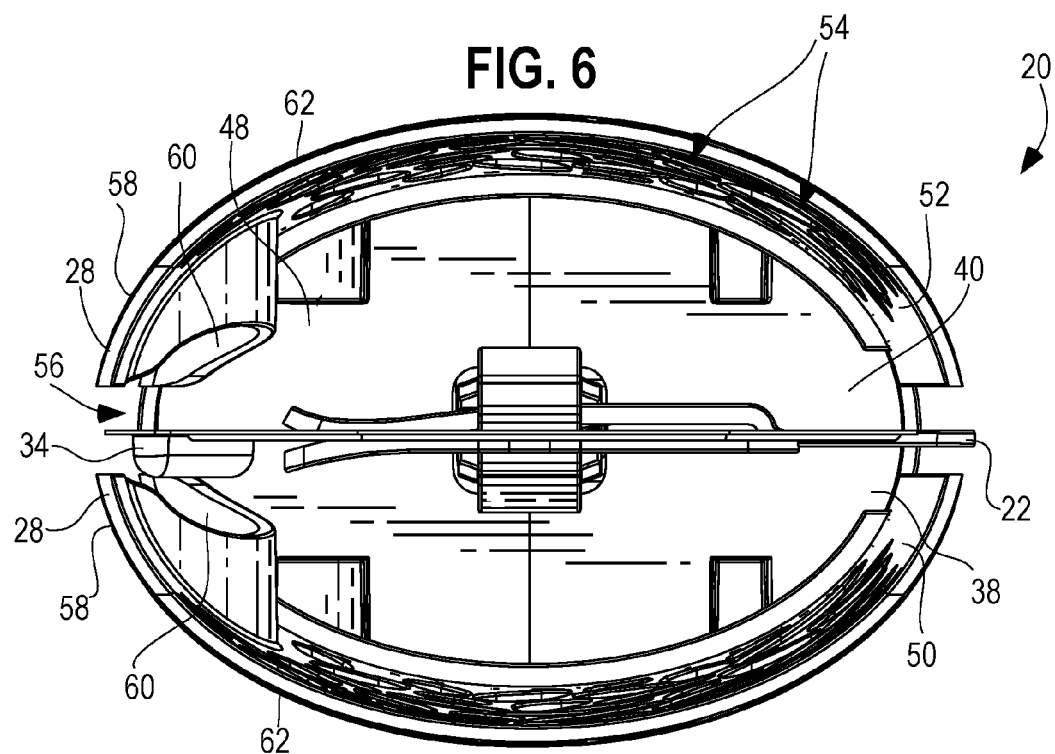
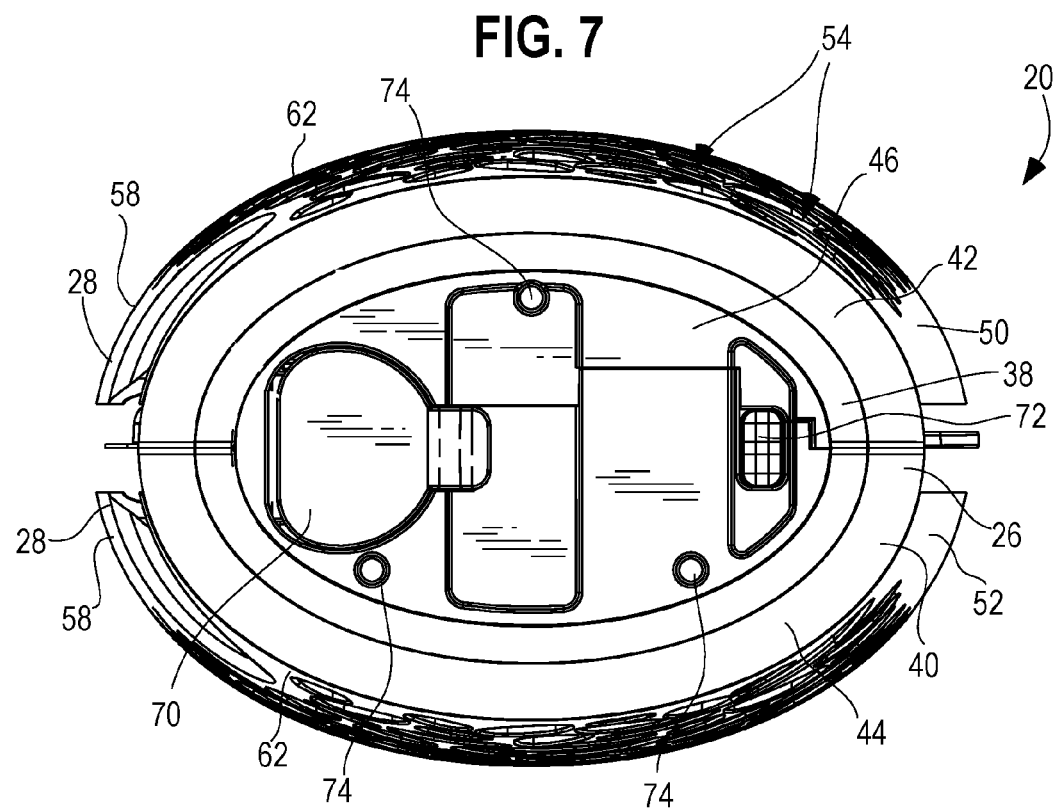

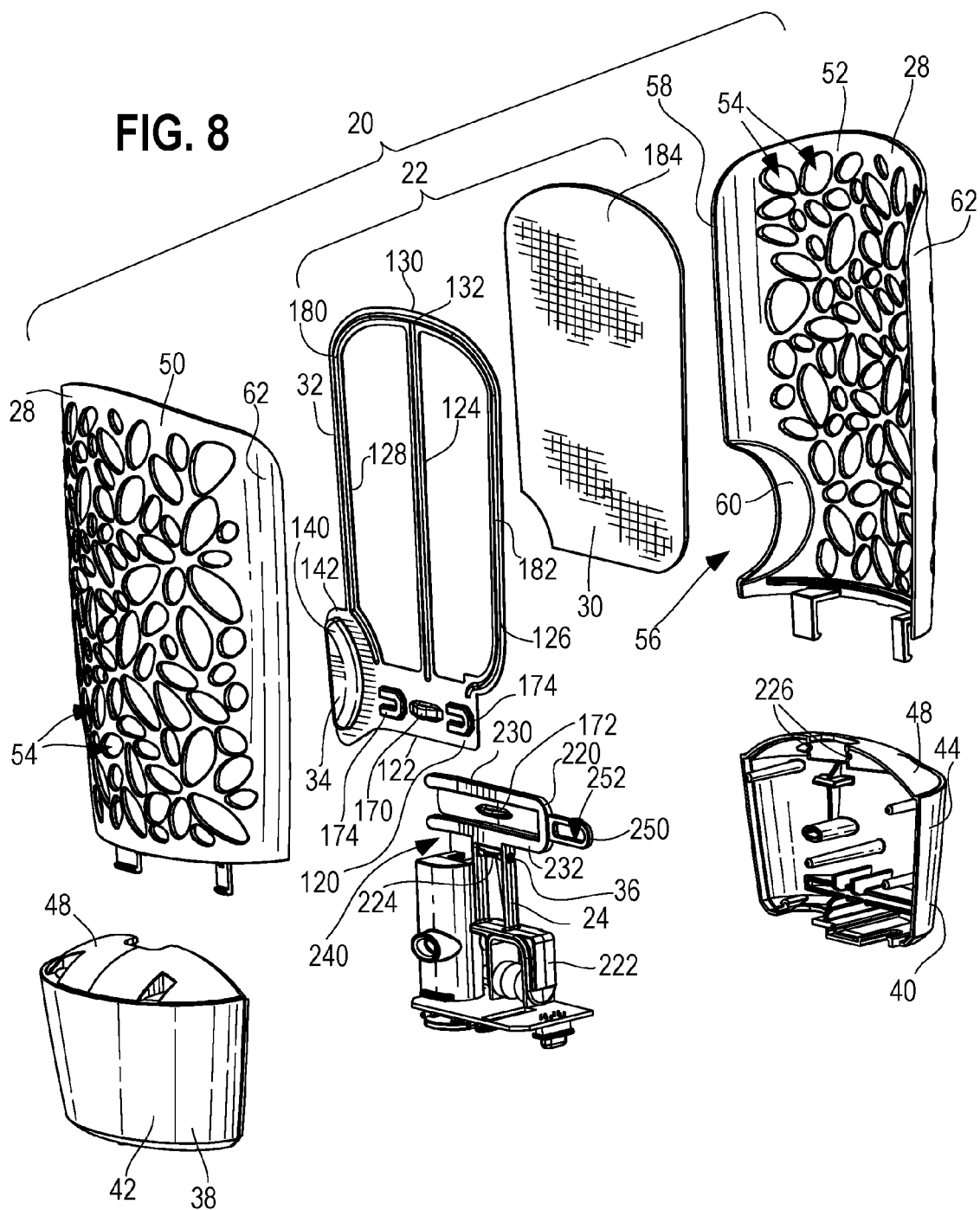

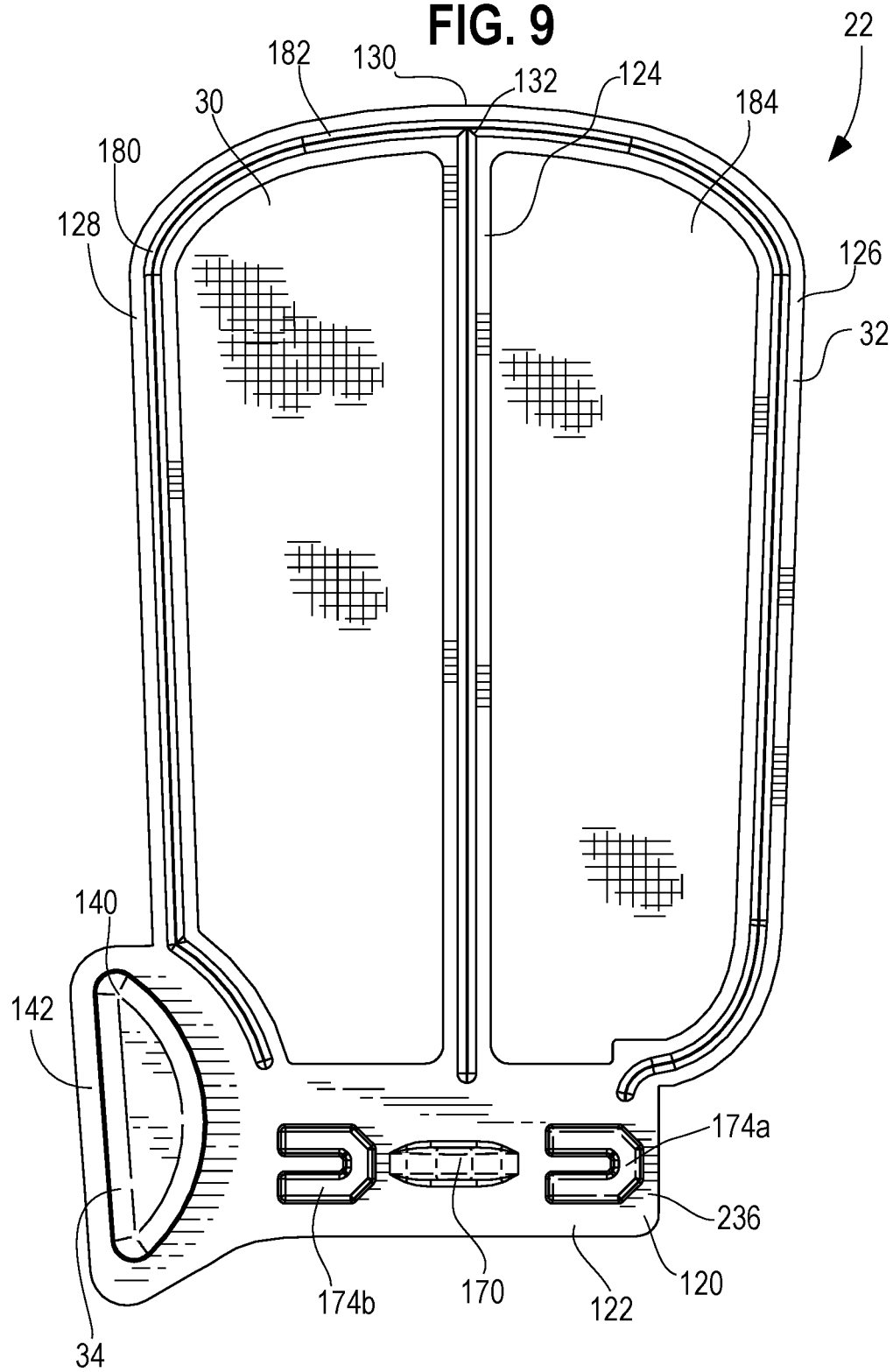

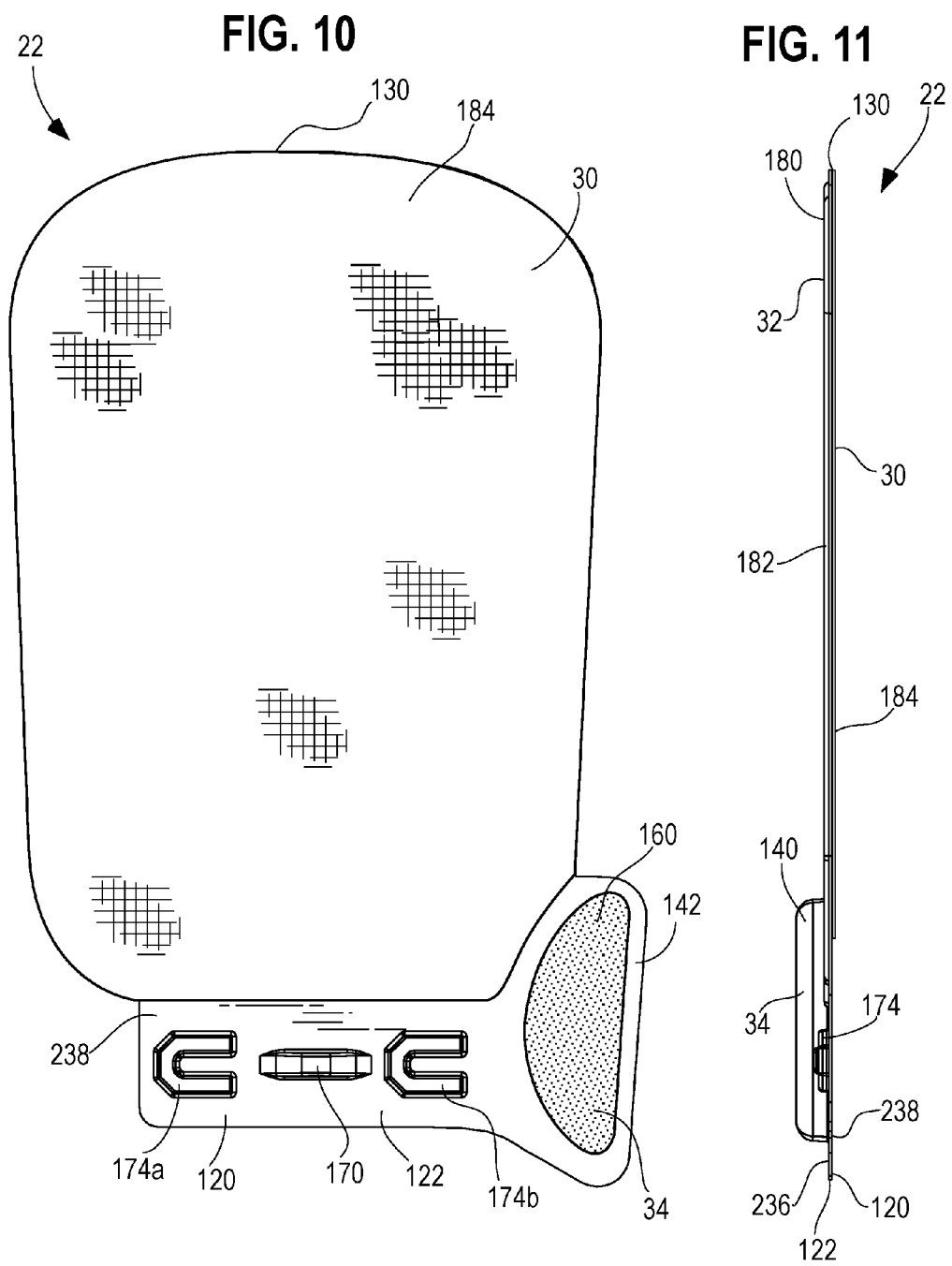

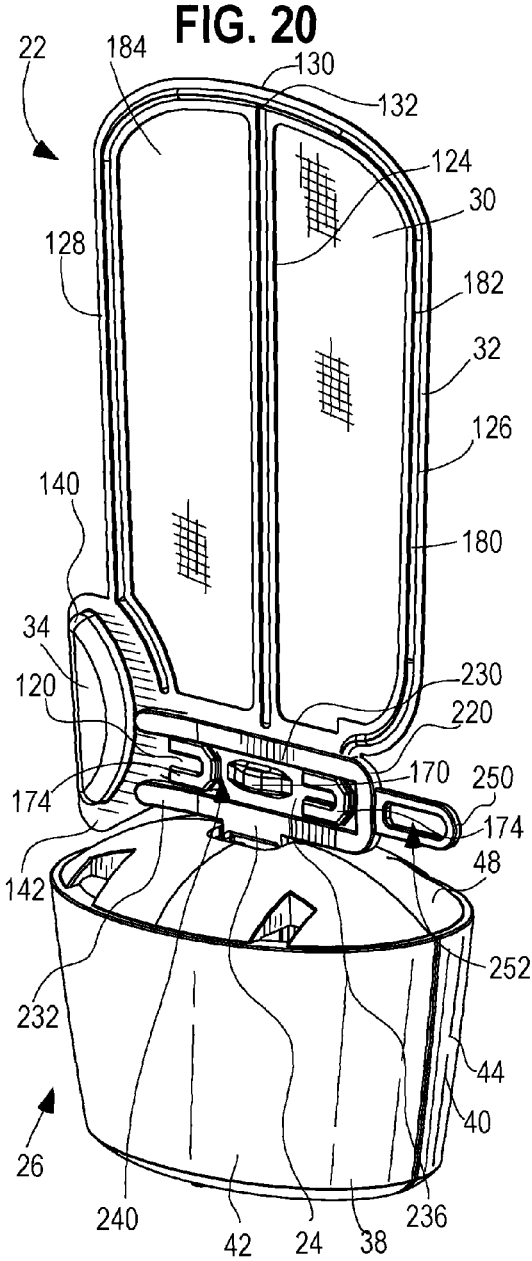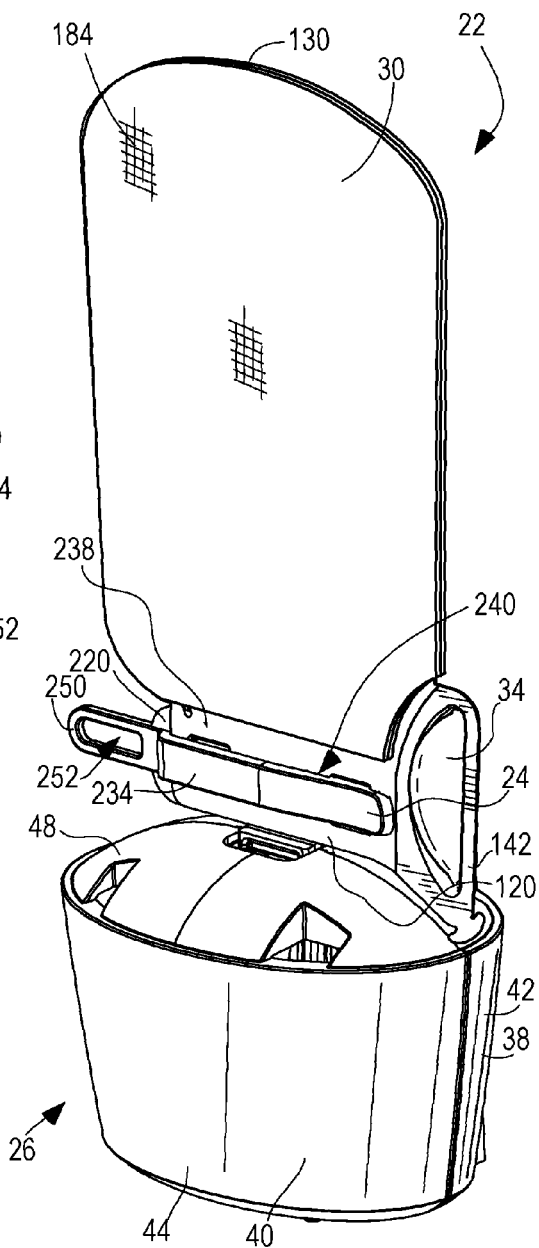

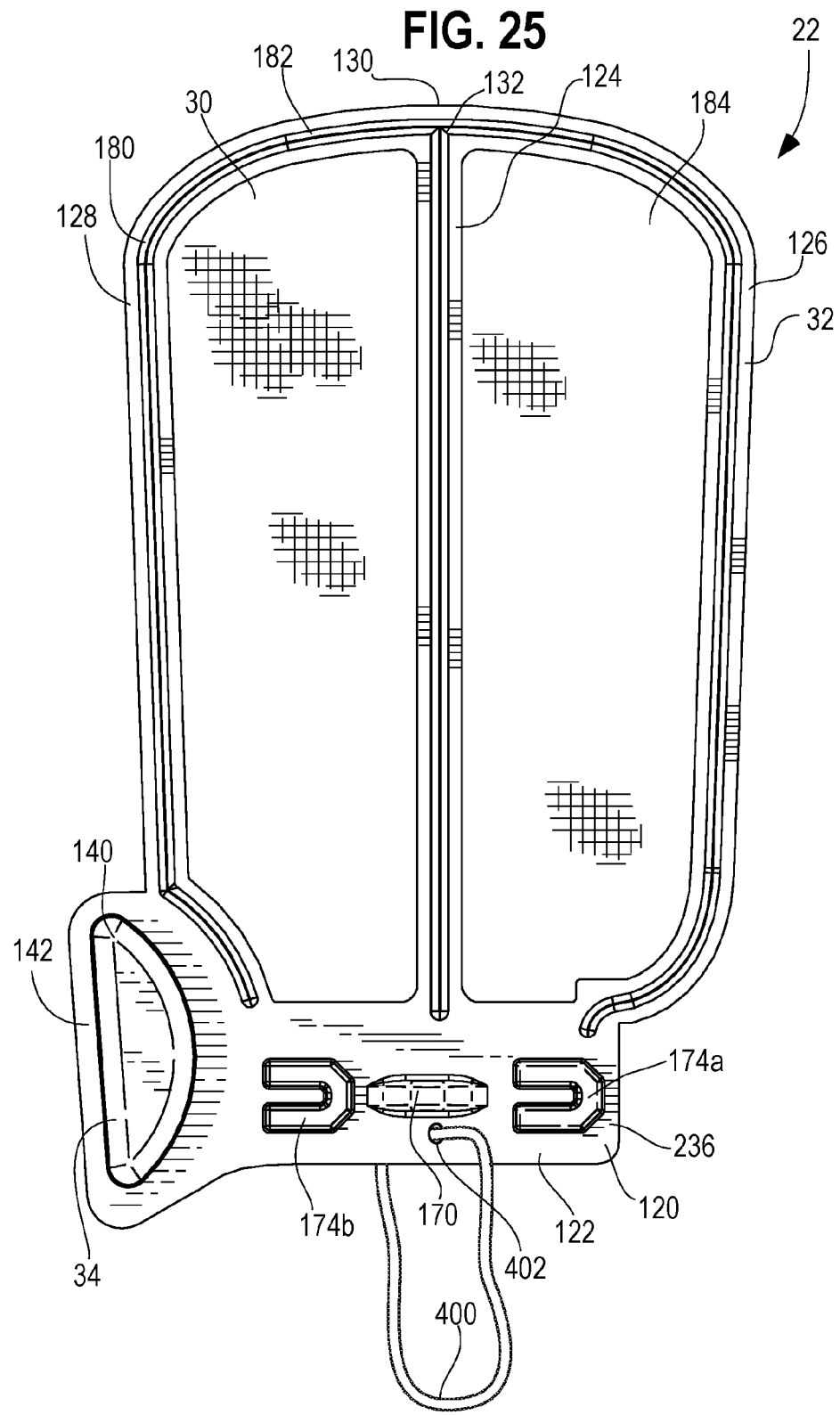

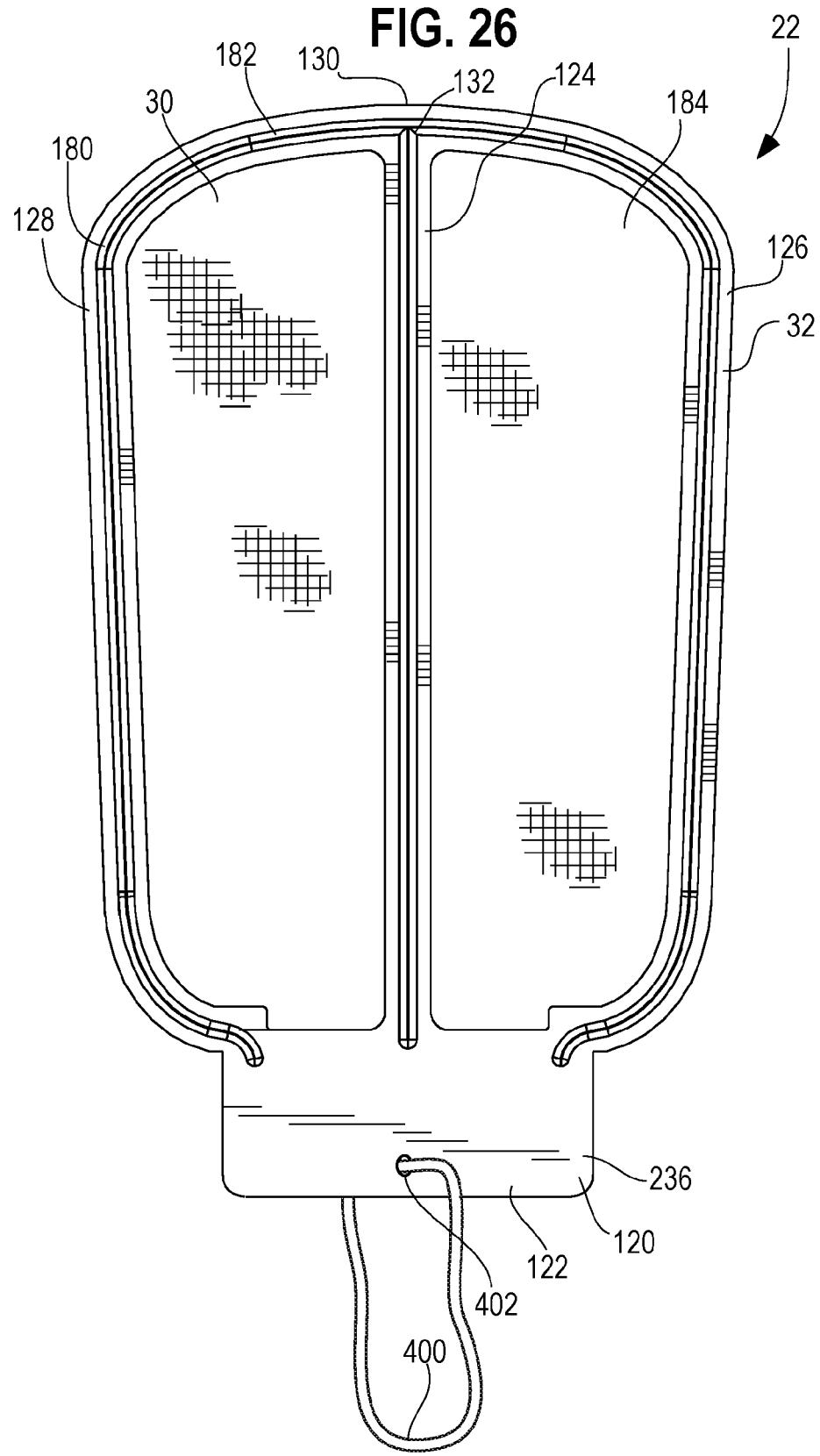

DISPENSING DEVICE

CROSS REFERENCE TO RELATED APPLICATIONS

None.

REFERENCE REGARDING FEDERALLY SPONSORED RESEARCH OR DEVELOPMENT

Not applicable.

SEQUENTIAL LISTING

Not applicable.

BACKGROUND OF THE DISCLOSURE

1. Field of the Disclosure

The present disclosure generally relates to a dispensing device having a substrate supported by a frame and, more specifically, to a dispensing device utilizing a magnetically driven arm coupled with a frame and substrate to promote air flow along the substrate.

2. Description of the Background of the Disclosure

Various volatile material dispensing devices are known in the prior art that generally comprise a reservoir that holds a volatile material and include a housing or support structure to retain the reservoir. The prior art dispensing devices allow passive diffusion of the volatile material to occur without the aid of a dispensing mechanism or enhance and/or facilitate the release of the volatile material using an active dispensing mechanism. Typical active dispensing mechanisms used in volatile material dispensing devices include a heating device and/or a fan.

Currently, numerous factors affect the efficacy of active and passive dispensing devices used to deliver a pest control agent, a fragrance, or other volatile compositions. For example, factors such as the overall volume of a space to be treated, the treatment radius (i.e., the linear distance from the dispensing device), the temperature, air currents, and the like may have an affect on the use and efficacy of the dispensing device.

Typically, volatile compositions are emitted into a target environment as one of an active, instant action composition that is efficacious for a short period of time upon release or as a passive, continuous action composition that is efficacious for a prolonged period of time. These various active and passive emanation systems each have advantages and drawbacks. For example, active systems enable a user to quickly release a desired amount of a pest control agent or fragrance into the environment to repel/knockdown insects or overcome a strong odor. However, these spikes in composition intensity usually decay rapidly. On the other hand, passive systems are longer lasting, but typically are not as concentrated and do not include an indicator that allows a user to determine when the volatile has been fully expended.

Therefore, it would be desirable to have the advantages of both active and passive systems. The present disclosure provides such advantages by combining a substrate typically found in passive systems with a long lasting active emanator in the form of a pendulum drive device that moves the substrate. Such systems provide airflow along the substrate that is charged with a volatile material to effect increased emanation therefrom. Further, the systems disclosed herein may also utilize a use-up cue to indicate to a user when the substrate requires a new charge of the volatile material or requires replacement. The present disclosure provides new and non-obvious dispensing devices, which address one or more of the above issues.

SUMMARY

According to one aspect, a dispensing device for release of a volatile material includes a base, a drive arm coupled to a pendulum based drive mechanism, and a refill coupled to the drive arm. The refill includes a support base, at least one flange, a substrate coupled with the at least one flange, and a use-up cue.

According to another aspect, a refill for dispensing a volatile material includes a support base, one or more flanges extending from the support base, one or more retention mechanisms disposed along the support base, a substrate coupled with the one or more flanges, and a use-up cue.

According to a different aspect, a refill for dispensing a volatile material includes a support base, at least one retention mechanism provided on the support base, a substrate coupled with the support base, wherein a volatile material is provided on the substrate, and one or more flanges provided along the substrate.

BRIEF DESCRIPTION OF THE DRAWINGS

FIG. 6 is a top plan view of the dispensing device of FIG. 1;

FIG. 7 is a bottom plan view of the dispensing device of FIG. 1;

FIG. 8 is a front isometric exploded view of the dispensing device of FIG. 1;

FIG. 9 is a front elevational view of a refill;

FIG. 10 is a rear elevational view of the refill of FIG. 9;

FIG. 11 is a left side elevational view of the refill of FIG. 9;

FIG. 20 is a front isometric view of the refill and drive arm of FIG. 18 coupled with a base;

FIG. 21 is a rear isometric view of the refill, drive arm, and base of FIG. 20;

FIG. 25 is a front elevational view of the refill of FIG. 9 with an attachment mechanism provided thereon; and FIG. 26 is a front elevational view of another embodiment of a refill similar to the one shown in FIG. 9 with an attachment mechanism provided thereon.

DETAILED DESCRIPTION OF THE DRAWINGS

Figure 1:
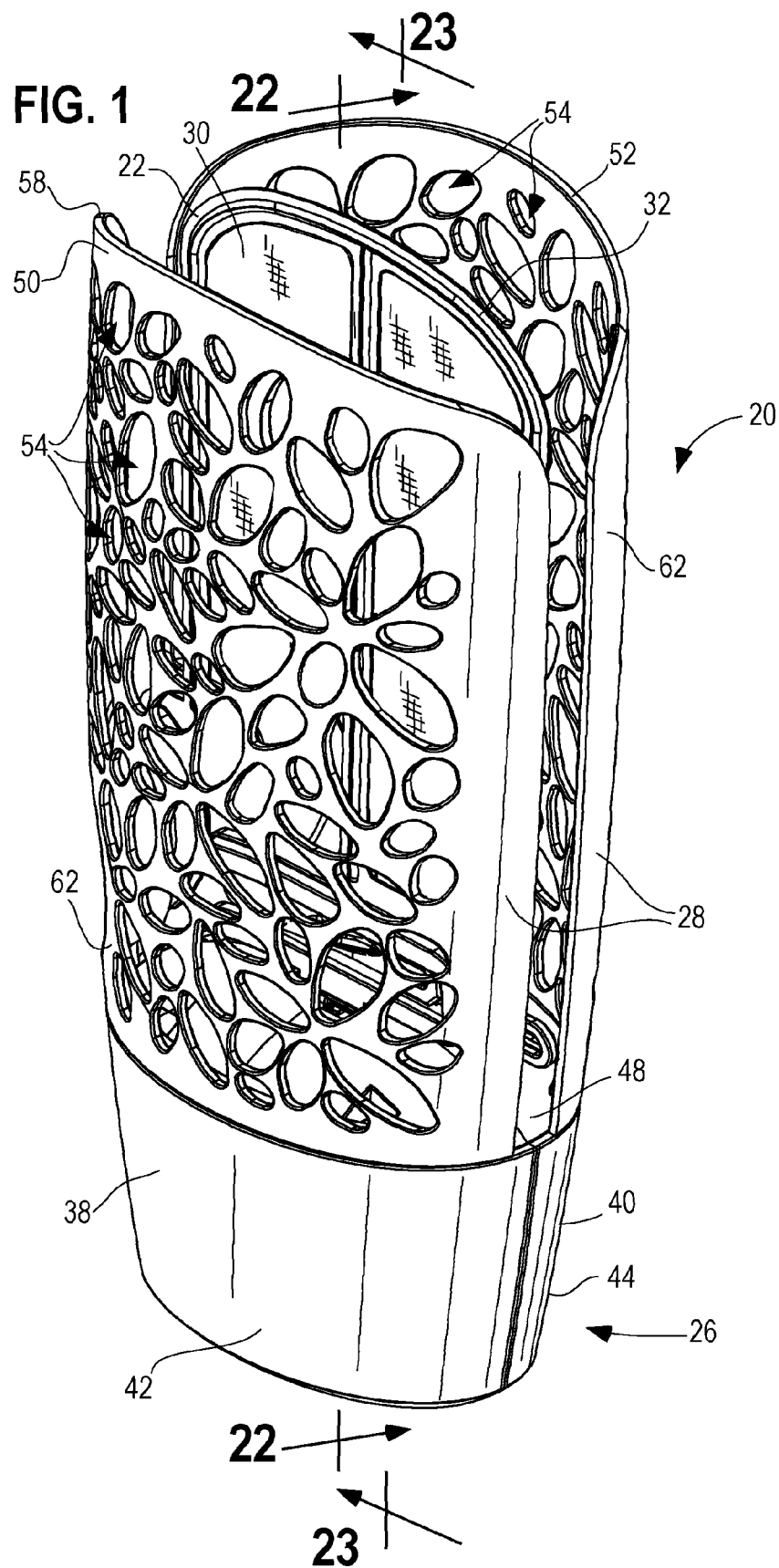
FIG. 1 is a front isometric view of a first embodiment of a dispensing device including a refill.

FIGS. 1-8 generally depict a dispensing device 20 for use in the emanation of a volatile material into the ambient environment. In one preferred embodiment, the dispensing device is used to emanate a pest control agent, such as a repellant or insecticide. The dispensing device 20 advantageously provides a visual cue to the user of the efficacy of a refill 22 used in the device, as well as visual feedback to the user that the device is operating through the movement of the refill by a drive arm 24 (see FIG. 8) controlled by electromagnetic forces.

Turning to FIGS. 1-7, a base 26 of the dispensing device 20 is shown to have two opposing surfaces extending therefrom that define a shroud or shade 28. The refill 22, which will be described in greater detail below, generally comprises a substrate 30, a frame 32, and a use-up cue 34. The refill 22 is retained within the shade 28 and is coupled to the drive arm 24. With reference to FIG. 8, the refill 22 and the drive arm 24 are in moveable communication with the base 26 about a pivot 36.

Still referring to FIG. 8, the base 26 comprises a first portion 38 and a second portion 40 that are coupled together. When coupled, the base 26 defines a front wall 42, a rear wall 44, a bottom wall 46, and a top wall 48. The front wall 42 and the rear wall 44 are generally curved and extend upward and outward from the bottom wall 46. Referring to FIGS. 6 and 7, the top wall 48 and the bottom wall 46, respectively, are generally oval shaped. However, the bottom wall 46 and/or the top wall 48 may be formed in any known shape, e.g., a circle, a square, a rectangle, a triangle, a pentagon, a hexagon, etc. Further, the footprints of the bottom wall 46 and the top wall 48 may be identical or similar, such that they define identical or similar geometric shapes of equal or differing size. In an alternative embodiment, the base 26 comprises a unitary or non-unitary structure that provides a void within an interior and for the communication of the drive arm 24 into the interior.

With reference again to FIGS. 1-8, the first portion 38 and the second portion 40 may be secured by a snap fit, an interference fit, magnets, adhesion, ultrasonic welding, or any other method of coupling known to those of ordinary skill in the art. Further, the shade 28 may be coupled to the base 26 in a similar or different manner. In a preferred embodiment, the shade 28 includes a first shade 50 and a second shade 52. As illustrated in FIGS. 1-7, the first shade 50 is coupled with the top wall 48 and flush with the front wall 42 of the base 26 and the second shade 52 is coupled with the top wall 48 and flush with the rear wall 44 of the base 26. However, the device 20 may include any number of shade attachments, such as a fewer number or a greater number than the two shown in the present embodiment. In one embodiment, the device 20 includes a single unitary shade attachment that is positioned around a periphery of the base 26. In another embodiment, the device 20 includes a single shade attachment that surrounds a portion of a periphery of the base 26. In a different embodiment, the shade attachment is non-removably inserted into the base 26. In yet another embodiment, no shade attachments are provided. In still a different embodiment, three or more shade attachments are provided that may, or may not, be equidistantly spaced around a periphery of the base 26. In any of the disclosed embodiments, the shade attachments may be integrally formed with the base 26, separately formed and removable from the base, or separately formed and not removable from the base. Still further, while the shade 28 is shown extending from the top wall 48 of the base 26, it is contemplated that the shade may extend from any portion of the base.

The first and second shades 50, 52 each include a plurality of flow apertures 54 disposed therein. In the present embodiment, the flow apertures are provided in a number of varying curvilinear shapes. In other embodiments, the flow apertures 54 may have the same shape or have differing geometric shapes. It is also contemplated that any of the embodiments may include flow apertures 54 of the same or differing size. In a preferred embodiment, the flow apertures 54 extend through between about 10% and about 90% of the surface area of the shade 28, and in another preferred embodiment between about 20% and about 80%, and in still another preferred embodiment between about 30% and about 70%. With respect to the present embodiment, both of the first and second shades 50, 52 include flow apertures 54 that extend through between about 10% and about 90% of the surface area thereof.

Figure 2:
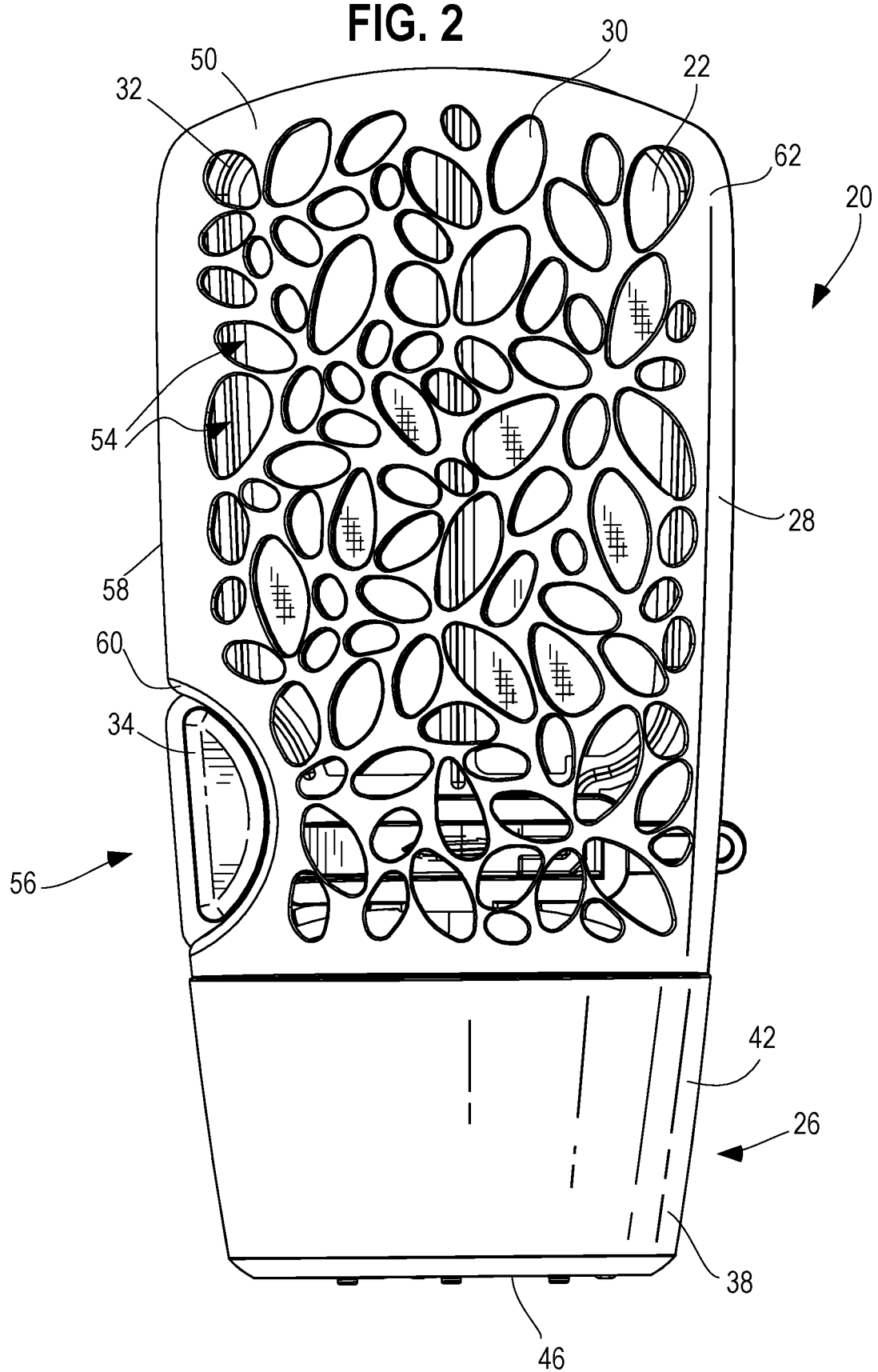
FIG. 2 is a front elevational view of the dispensing device of FIG. 1.
Figure 3:
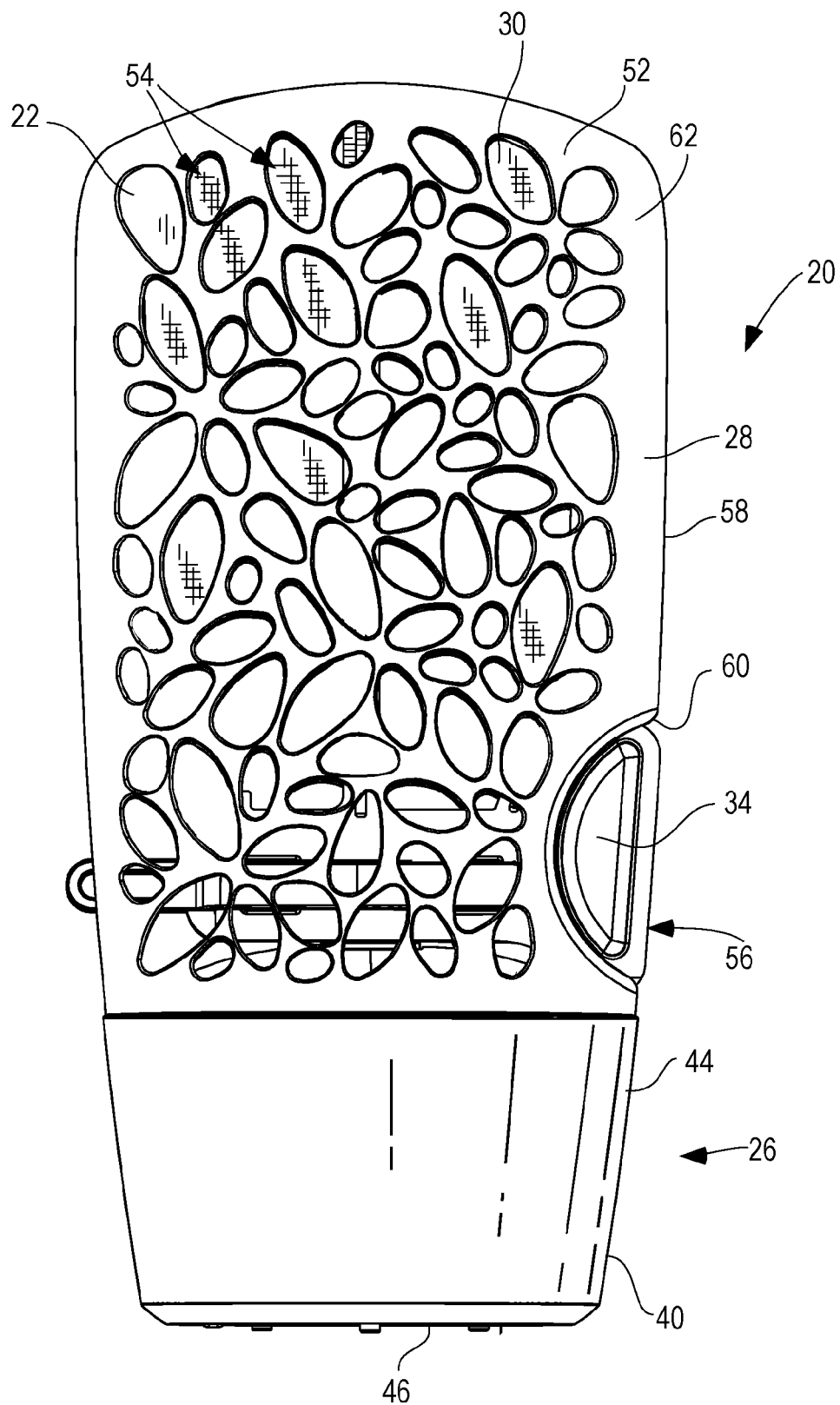
FIG. 3 is a rear elevational view of the dispensing device of FIG. 1.
Figure 4:
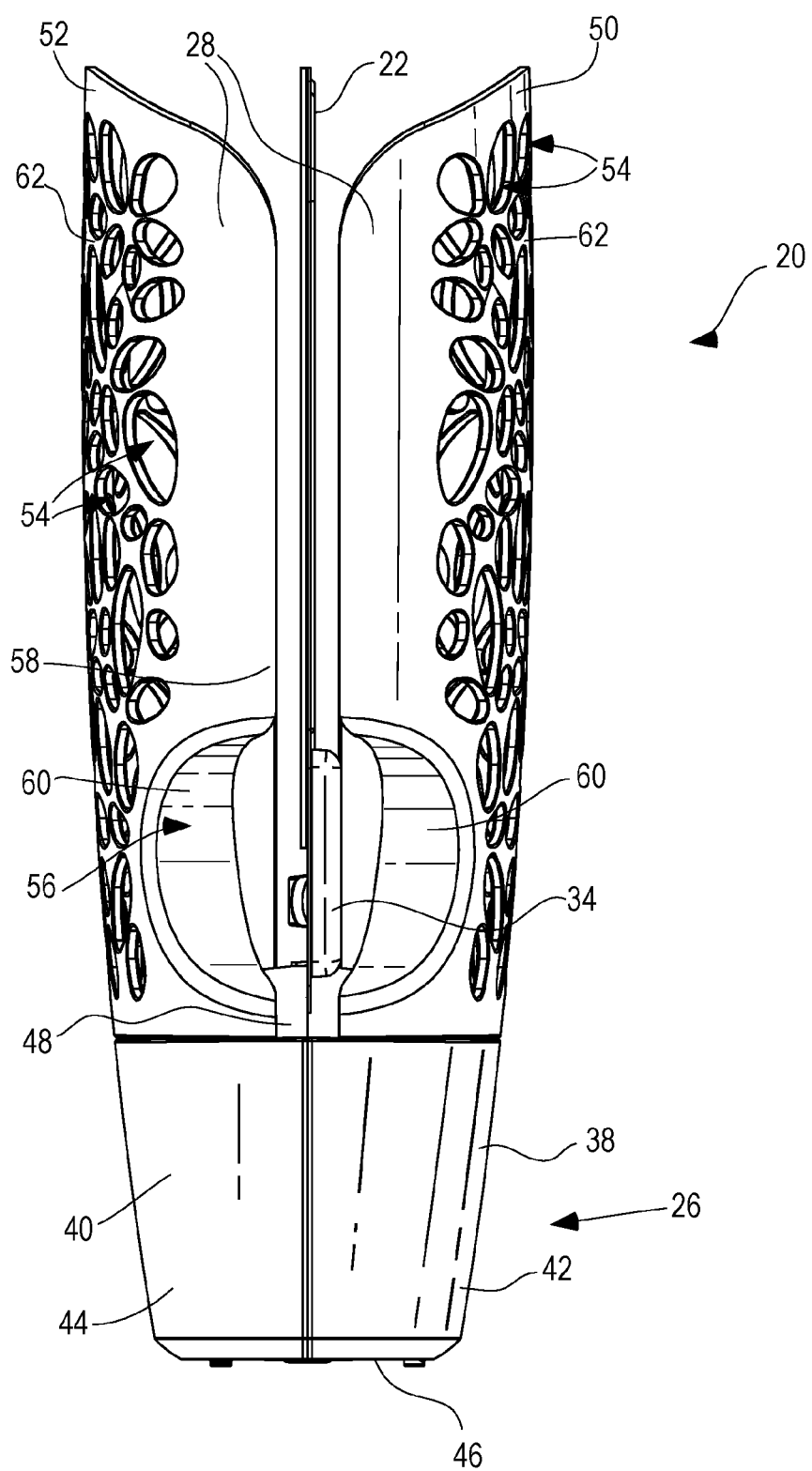
FIG. 4 is a right side elevational view of the dispensing device of FIG. 1.
Figure 5:
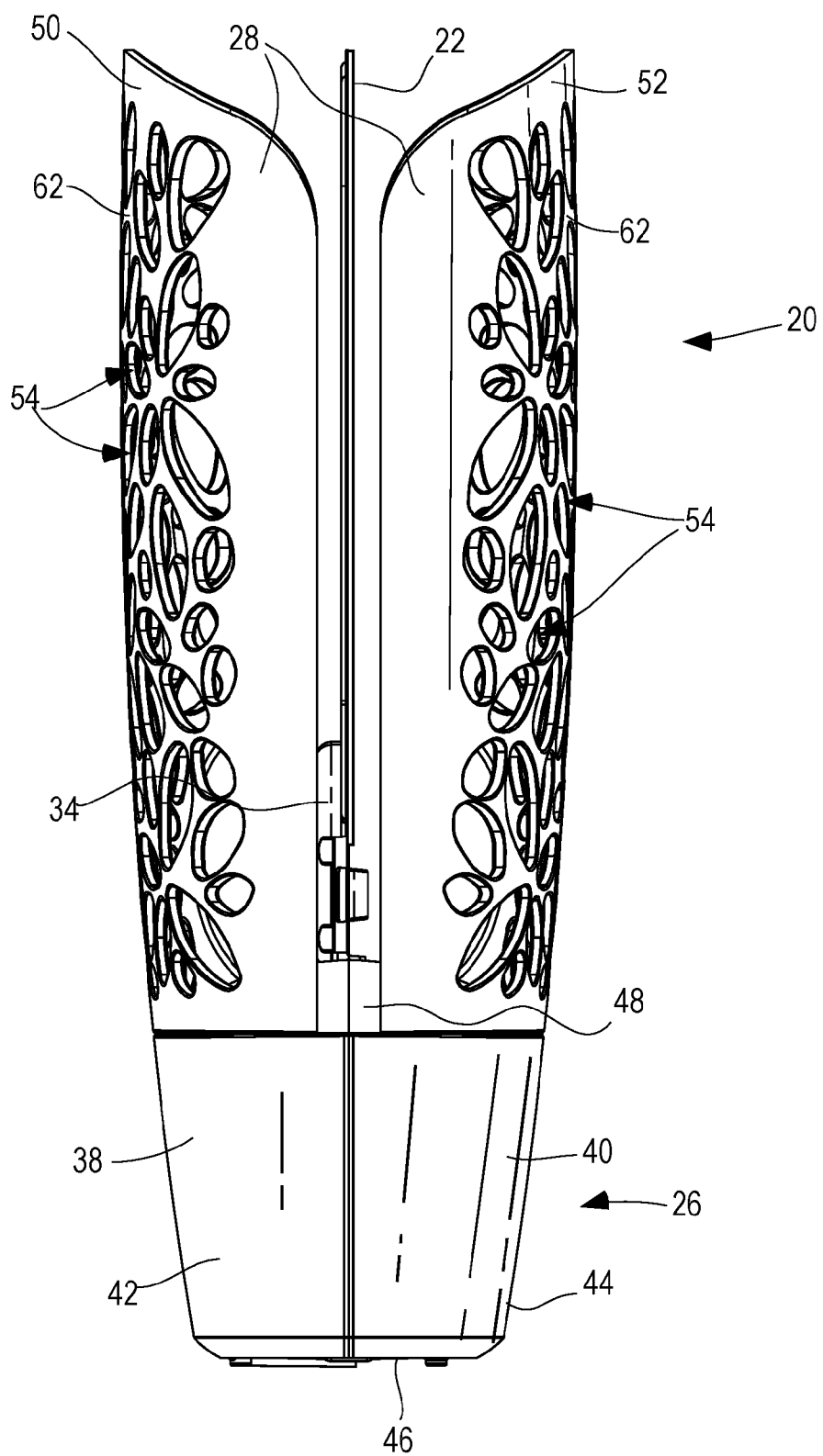
FIG. 5 is a left side elevational view of the dispensing device of FIG. 1.
Figure 12:
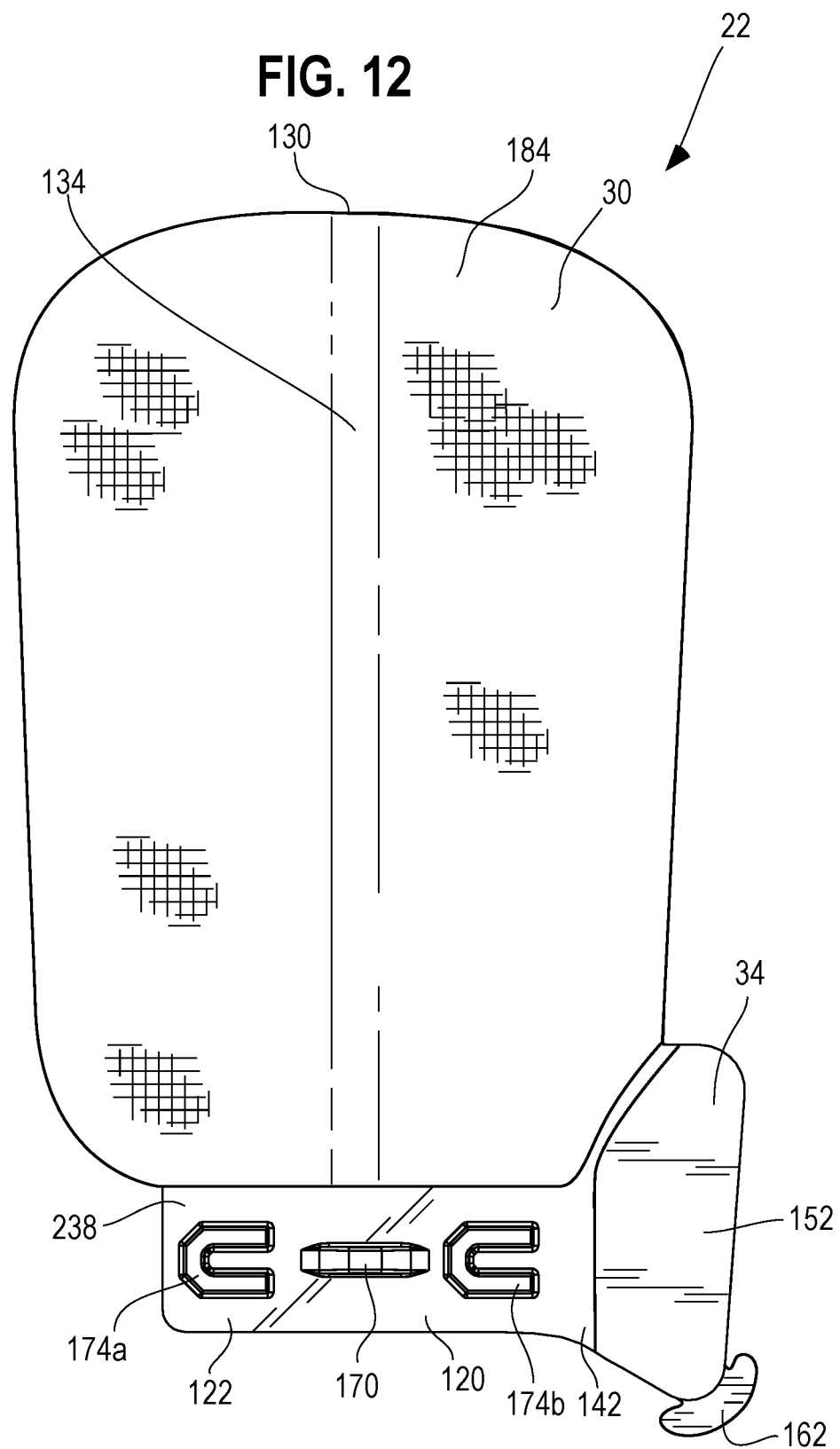
FIG. 12 is a rear elevational view of another embodiment of a refill that includes a region of rigidity and a peel-off film.

Turning to FIGS. 2-4, the first shade 50 and the second shade 52 have a cut out 56 along a side 58 thereof. In some embodiments, the shade 28 has another cutout at a different location. The cut out 56 is generally formed in the same shape as the use-up cue 34. The cut out 56 allows a user to readily see the use-up cue 34 to determine a fill level thereof. The cut out 56 also allows a user to easily remove the refill 22 from the dispensing device 20. In a preferred embodiment, the cut out 56 has a generally circular or otherwise curvilinear shape, which truncates the shade 28 to define a cut out surface 60 (see FIG. 4) that extends from an outward facing side 62 of the shade 28 toward an interior side adjacent the refill 22. In other embodiments, the cut out 56 does not include a cut out surface 60. In still further embodiments, the cut out surface 60 may be one or more surfaces, may be planar, may have surface indicia inscribed thereon, or may have any number of aesthetic and/or functional features to assist the user in viewing and/or manipulating the refill and use-up cue 34. While the first and second shades 50, 52 of the present embodiment are mirror images of one another, other embodiments need not be. For example, one of the first or second shades 50, 52 may include the cut out 56 while the other does not.

Referring to FIG. 7, disposed along the bottom wall 46 of the base 26 is a door 70 with a latch, a power switch 72, and one or more stabilizing feet 74. The door 70 is hinged to the bottom wall 46 to allow a user to open the door 70, insert the energy source, which may be a battery as will be described in greater detail hereinafter below, and close the door 70 and latch to retain the energy source within the base 26. The switch 72 turns the dispensing device 20 on and off. The one or more stabilizing feet 74 provide stability for the dispensing device 20 when the device is resting on a flat surface. The dispensing device 20 may include more or fewer stabilizing feet 74 depending on the intended use of the device 20 or user preferences.

Referring now to FIGS. 9-17, the frame 32 of the refill 22 includes a support base 120 disposed at a bottom end 122 of the refill 22. A center flange 124, a left flange 126, and a right flange 128 extend upward from the support base 120 toward a top end 130 of the refill 22. The center flange 124, the left flange 126, and the right flange 128 intersect at a flange intersection 132. In some embodiments, the center flange 124 and/or the left flange 126 and/or the right flange 128 have a curvature applied thereto for structural or aesthetic purposes. The use-up cue 34 extends outward from the right flange 128.

It is also contemplated that variations in flange numbers and/or shape may be desirable depending on the intended functionality of the dispensing device 20 and user preferences. In some embodiments, the substrate 30 includes less than three flanges, for example, one flange or two flanges. In other embodiments more than three flanges are provided, such as four or five or six or more flanges. In other embodiments, the substrate 30 does not include any of the flanges 124, 126, 128, but rather includes a region of rigidity 134 (see FIG. 12) that provides the structural support for the substrate 30 to stand vertically and undulate when the dispensing device 20 is turned on. In other embodiments, the substrate 30 includes two or more regions of rigidity 134. Such regions of rigidity 134 may comprise numerous structures, e.g., a fold in the substrate 30, a region of thicker material in the substrate, an added material to a portion of the substrate that may be the same or different than the material comprising the substrate, an adhesive or other modifier that adds rigidity to a portion of the substrate, etc. Regardless of the particular means to effect the region of rigidity 134, it may be generally characterized as an area of the substrate 30 that is more rigid than another area of the substrate.

It is intended that variations in the shape of the flanges also may provide the designer and user flexibility in the manner in which the refills 22 are fashioned to effect the proper functionality of the dispensing device 20. For example, in one embodiment the center flange 124 is a Y-shaped flange that extends from the support base 120 upward and forks toward upper corners of the left flange 126 and the right flange 128, respectively. Further, in some embodiments, only the center flange 124 is included. In other embodiments, only the left flange 126 and the right flange 128 are included. Any of the flanges 124, 126, 128 may extend an entire length of the substrate, or may extend a partial length of the substrate, as will be discussed in greater detail below.

Contemplated variations in the shape and number of flanges allows for the balance between aesthetics and functionality in the refill 22. Indeed, it is anticipated that many modifications may be made to provide variations to users during the use of a single dispensing device 20, for example, seasonal offerings or multiple design offerings to allow user selection of a desirable refill 22 for their dispensing device 20 and area of intended use. While such design variation is anticipated, the refill 22 must also include appropriate flange numbers and shapes to impart sufficient rigidity to the substrate 30 so that it stands upright during a non-use state. Preferably, sufficient rigidity is imparted to the refill 22 so that no portion impacts any other part of the base 26 or shade 28 during use. More preferably, the refill 22 is provided with flange numbers and sizes to allow the refill 22 to be sufficiently rigid to not touch portions of the dispensing device 20 during use, but still allow the substrate (and flanges) to undulate in a wave-like pattern. Such a pattern may take on many variations, but may be generally understood to provide some form of flexing motion about all or a portion of the substrate 30 when the drive arm 24 is moving.

Figure 13:
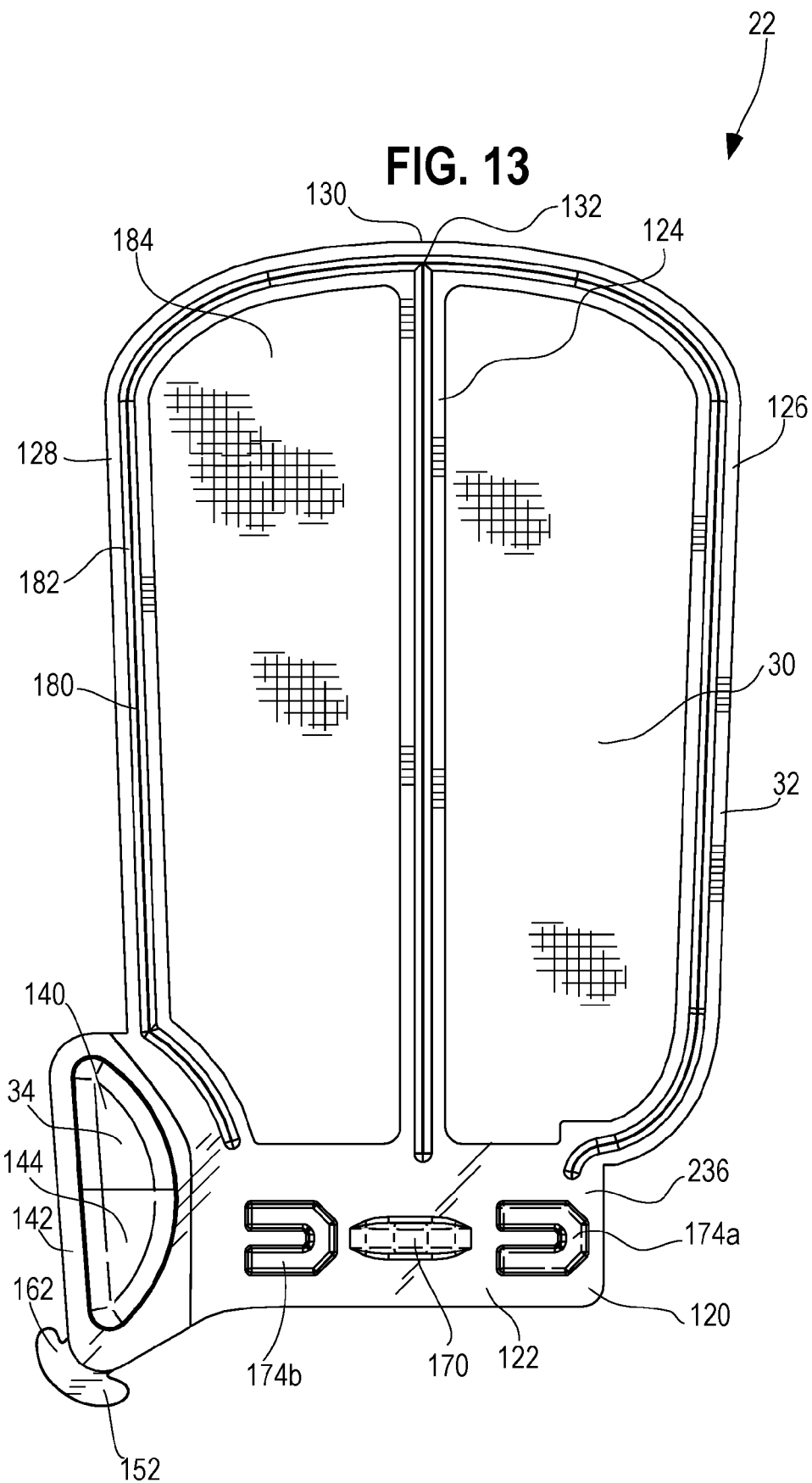
FIG. 13 is a front elevational view of the refill of FIG. 12.
Figure 14:
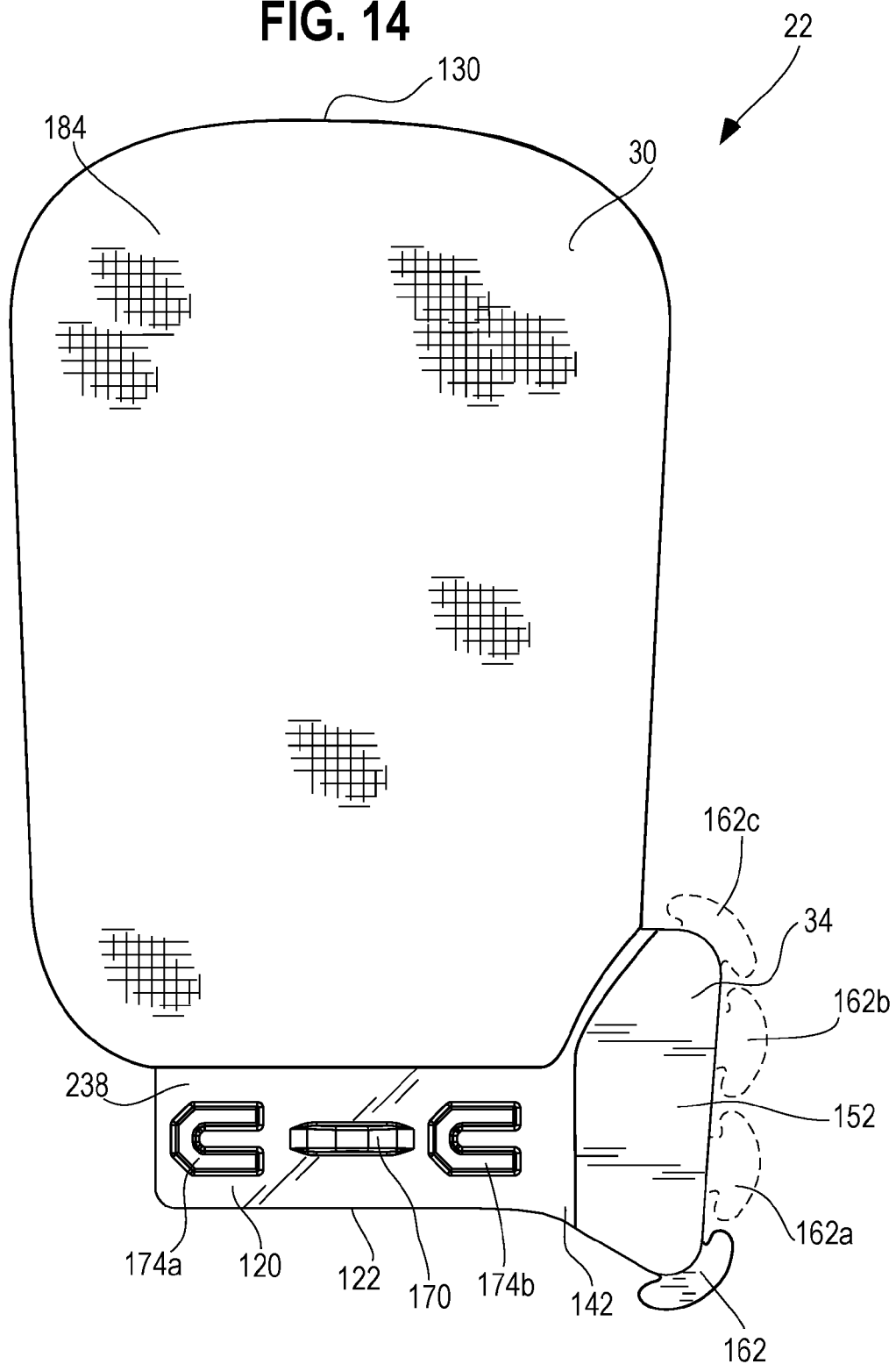
FIG. 14 is a rear elevational view a different embodiment of a refill having alternate positions for a peel-off tab.
Figure 15:
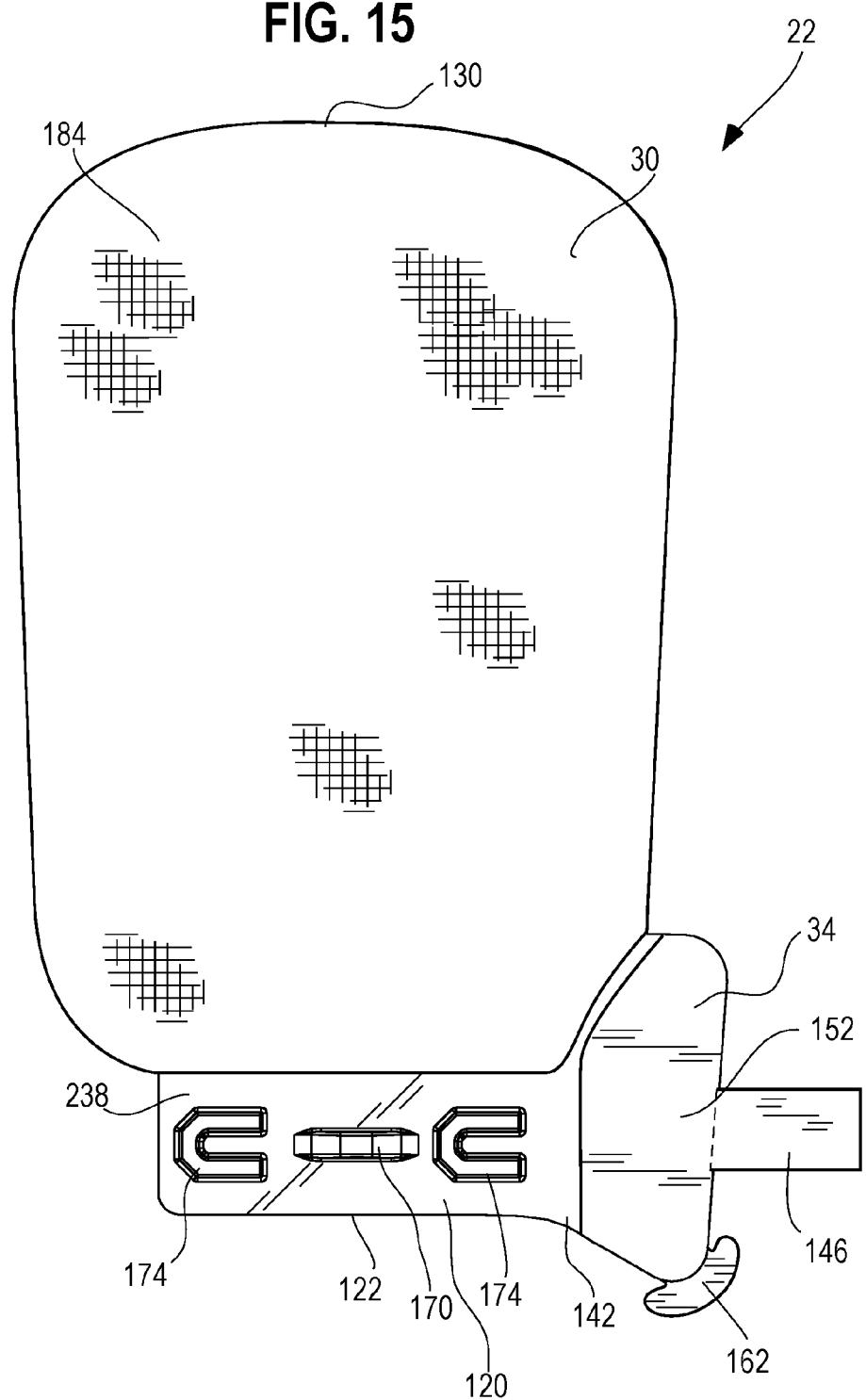
FIG. 15 is a rear elevational view of another embodiment of a refill that includes a peel-off film and an outwardly extending frangible portion.
Figure 16:
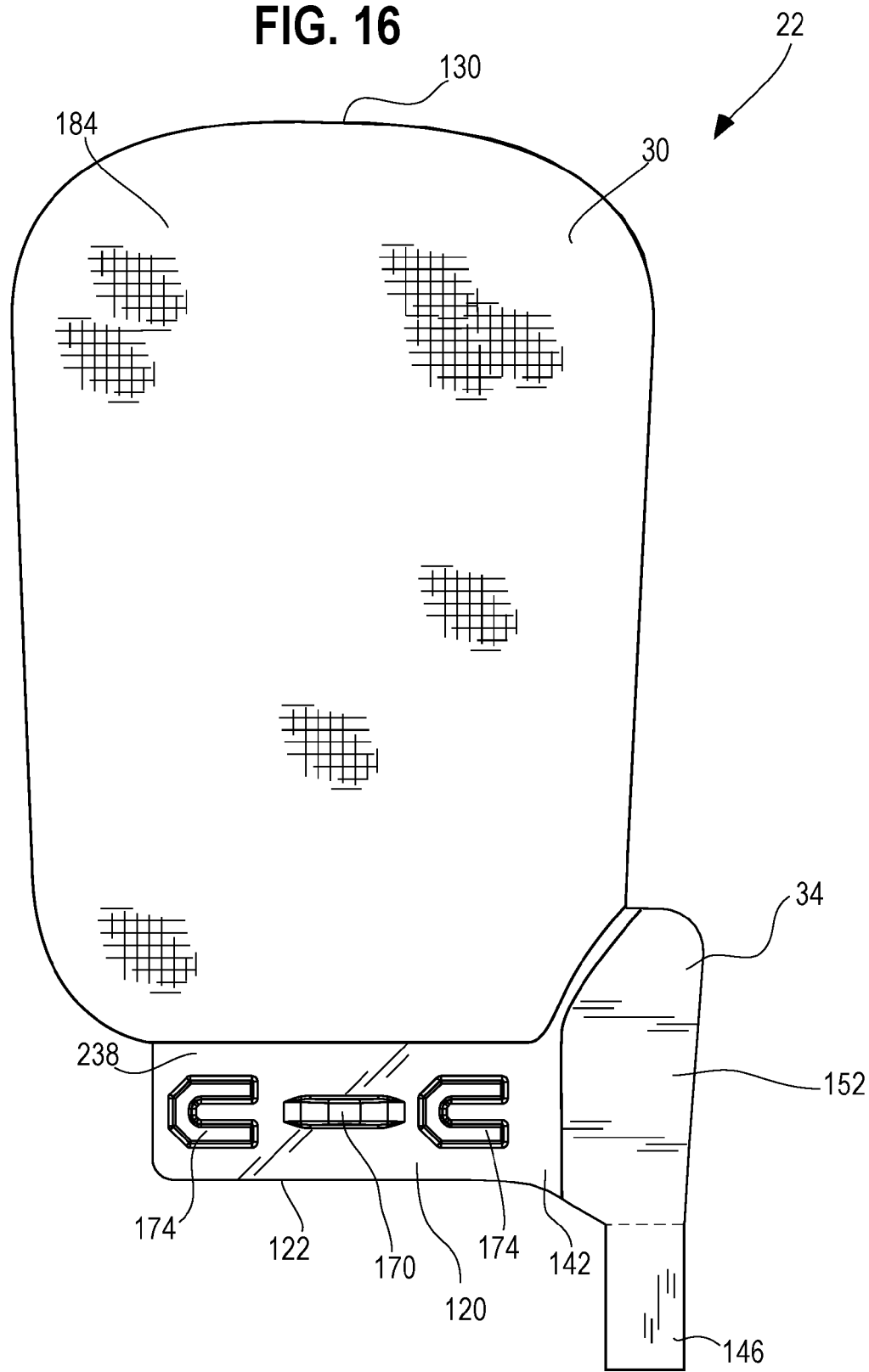
FIG. 16 is a rear elevational view of yet another embodiment of a refill that includes a peel-off film and a downwardly extending frangible portion.

Still referring to FIGS. 9-17, the use-up cue 34 includes a reservoir 140 having a peripheral use-up cue flange 142. In the present embodiment, the reservoir 140 has a generally half-oval shape. In other embodiments, the reservoir 140 may be formed to have any shape. For example, the reservoir 140 may be in the shape of a circle, an oval, a triangle, a square, etc. Disposed within the reservoir 140 is an indicator material 144 (see FIG. 13). As illustrated in FIGS. 15 and 16, in some embodiments the use-up cue 34 further includes a frangible portion 146. In a preferred embodiment, the frangible portion 146 is removed by the user prior to operation of the dispensing device 20, as will be described in greater detail below. In some embodiments, the frangible portion 146 and/or a removable portion of the use-up cue 34 (for example, a removable impermeable membrane or laminate) must be removed before the refill 22 can be coupled with the drive arm 24 of the dispensing device 20 (see FIG. 16). In such embodiments, the frangible portion 146 or removable portion of the use-up cue 34 would interact with portions of the base 26 or shade 28 if the user attempted to insert the refill 22 without removing them. For example, in one embodiment, portions of the use-up cue 34 would impact portions of the cut out surface 60 or adjacent portions of the top wall 48.

Figure 17:
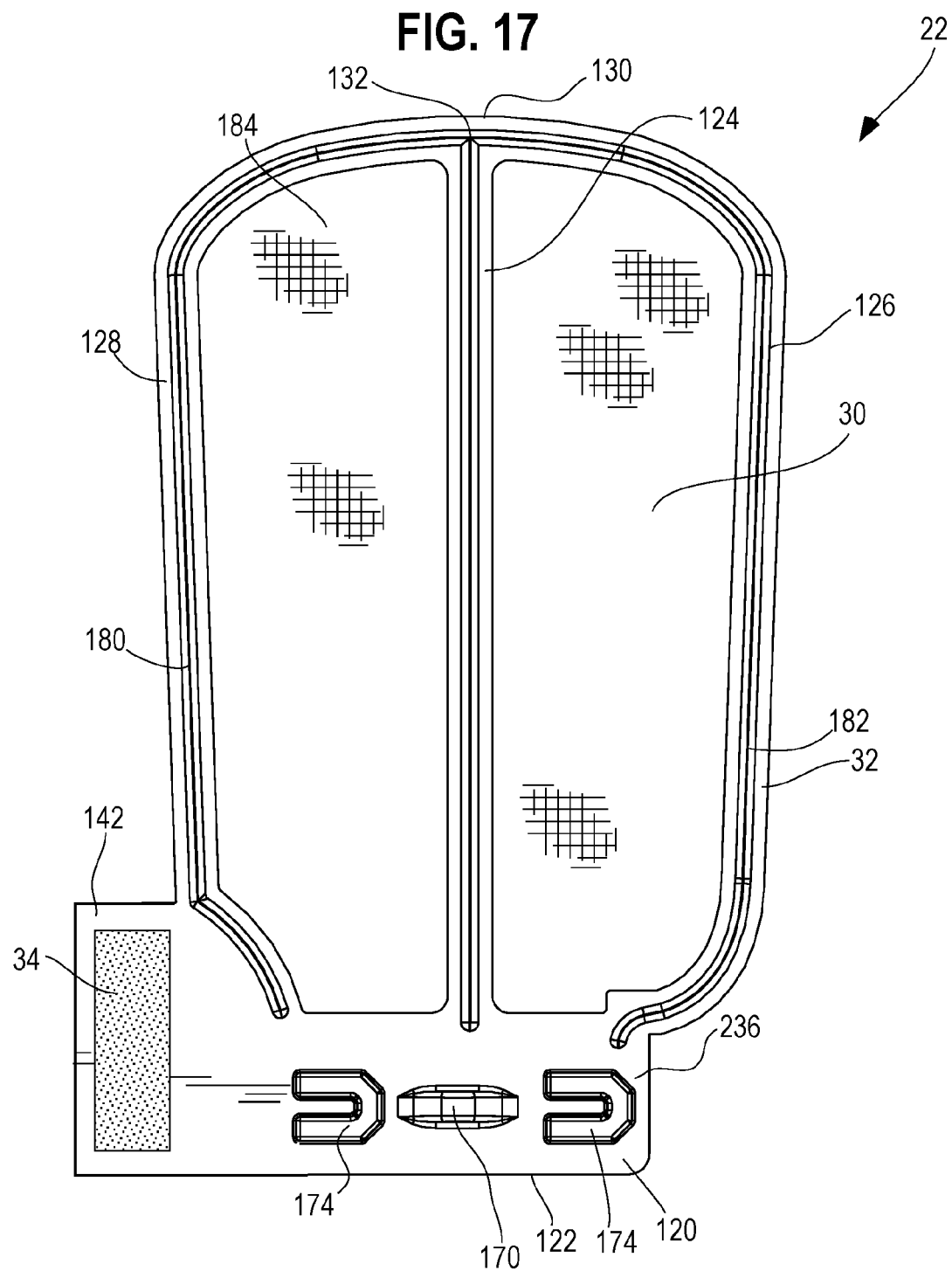
FIG. 17 is a front elevational view of still another embodiment of a refill.

FIGS. 9-12 show one type of elongated use-up cue 34 which includes the reservoir 140, a peel-off cover or impermeable membrane 152 (see FIG. 12), and a semi-permeable membrane 160. The peel-off cover 152 is removed when the refill 22 is first placed in use so as to expose the semi-permeable membrane 160 that covers the indicator material 144, thereby exposing the indicator material 144 to the environment. The indicator material 144 thereafter diffuses through the semi-permeable membrane 160 in a manner that is timed to the efficacy of the volatile material provided on the substrate 30. Once the indicator material 144 has completely (or substantially) volatilized, the substrate 30 (and the refill 22) should be replaced or recharged. As illustrated in FIGS. 12-15, the peel-off cover 152 has a tab section 162 extending outward past the use-up cue flange 142 to facilitate gripping of the peel-off cover 152. As illustrated in FIG. 17, the use-up cue 34 may take on other shapes than those illustrated in FIGS. 9-16. Further, the use-up cue 34 may be positioned at any point on the refill 22.

The indicator material 144 may be a liquid or a flowable gel. The indicator material 144 may be passively volatile (i.e., it volatizes by simply being exposed to the environment), or instead be largely or solely volatilized by a means such as a heater, a fan, airflow, or some combination thereof. Most preferably, the indicator material 144 is a colored liquid to facilitate viewing.

The peel-off cover 152 is preferably impermeable to the volatile material that comprises the indicator material 144. For example, a thin metal film or impermeable plastic may be used. In some embodiments, the peel-off cover 152 is configured to be reapplied to the use-up cue 34 to stop (or substantially stop) the indicator material 144 from diffusing though the semi-permeable membrane 160. In such instances, it is also anticipated that the substrate 30 will be sealed to prevent emanation of the volatile material therefrom to maintain the validity of the use-up cues 34 functionality in indicating to a user that the substrates efficacy has diminished to a point where it should be replaced. The tab section 162 of the peel-off cover 152 may be included along any portion of the use-up cue 34, as illustrated in FIG. 14 with tab sections 162a, 162b, and 162c. In fact, such tab sections 162-162c may comprise a portion of the refill 22 that interacts with surfaces of the base 26 or shade 28 to prevent insertion into the dispensing device 20 if not removed prior to use, as discussed above.

The reservoir 140 and/or the use-up cue flange 142, may be made from a wide variety of well known polymeric materials, including, for example, polyethylene, low density polyethylene, high density polyethylene, polyethylene terephthalate, polycarbonate, polypropylene, or any other material known to those of ordinary skill in the art. The peel-off cover 152 also may comprise a variety of known materials, including, for example, one or more of a polyester layer, a low density polyethylene layer, an aluminum foil layer, a polypropylene layer, and a low density polyethylene layer. Alternatively, the peel-off cover 152 may be replaced by some other covering mechanism, such as a rigid cover, so long as it can be removed or opened without damage to the semi-permeable membrane 160. Such alternative covers could simply be removed or could slide to one side, be hinged, or otherwise be configured so as to be openable and even to be reclosable.

A variety of semi-permeable membranes are possible to be used as the semi-permeable membrane 160, such as those of natural, semisynthetic, or synthetic origin. Examples include polyethylene, polypropylene, ethylene/vinyl acetate copolymer, polyvinyl chloride, polyurethane films, and combinations thereof.

Referring again to the frame 32, as illustrated in FIGS. 9-17, the support base 120 includes a groove 170 that interacts with a protrusion 172 (see FIG. 8) disposed on the drive arm 24. The groove 170 and the protrusion 172 act as retention mechanisms, which matingly receive one another. In some embodiments, the support base 120 and the drive arm 24 include more than one groove and protrusion, respectively. In other embodiments, the refill 22 may be coupled with the drive arm 24 via a snap fit, an interference fit, adhesion, magnets, ultrasonic welding, or any other method of coupling known to those of ordinary skill in the art.

The support base 120 further includes one or more support indentations 174. The support indentations 174 in the present embodiment include a left support indentation 174a and a right support indentation 174b. The support indentations 174 also act as retention mechanisms for the refill 22. In some embodiments, more than two support indentations 174 are included. In some embodiments, only a single support indentation 174 is included. In other embodiments, the support indentations 174 may be similar to the above-noted alternative retention mechanisms. In the illustrated embodiment, the center portion of each of the support indentations 174 is not indented, but rather is flush with the support base 120. As such, the support indentations 174 are horseshoe shaped or U-shaped and further include the functional benefit of guiding the refill 22 into place within the drive arm 24 during an insertion step as will be described in greater detail below.

In some embodiments, the support indentations 174 are other shapes. For example, the support indentations 174 may be in the shape of a triangle, a square, a rectangle, a hexagon, or any other polygonal shape. Still further, the support indentations 174 may be generally in the shape of an equal sign. Further, the support indentations 174 may have a center portion indented or flush with the support base 120. For the purposes of this disclosure, while an element may be referred to as being indented, this may be synonymous with being protruding. For example, given the relative thickness of the support base 120, an element such as the indentations 174 or groove 170 may extend outward from one side of the base 120 and inward from an opposing side of the base.

The support base 120 and/or the flanges 124, 126, 128 of the refill 22 may be made of a natural or a synthetic fibrous material. In one embodiment, the support base 120 and/or the flanges 124, 126, 128 comprise paper, cardboard, paperboard, or the like. In a different embodiment, the support base 120 and/or the flanges 124, 126, 128 comprise a lower density polymer. In yet a different embodiment, the support base 120 and/or the flanges 124, 126, 128 comprise other polymer and/or polymer blends such as polypropylene, polyethylene, and/or polyethylene terephthalate. Suitable materials have a grammage of between about 100 $g/m^2$ to about 500 $g/m^2$, or between about 200 $g/m^2$ to about 400 $g/m^2$, or about 300 $g/m^2$. It is envisioned that the support base 120 and/or the flanges 124, 126, 128 may comprise other materials so long as the material is rigid enough to provide support to the substrate 30. As previously noted, the refill 22 may not include any flanges 124, 126, 128, but may instead include one or more regions of rigidity 134.

As illustrated in FIGS. 9, 13, and 17, the center flange 124, the right flange 128, and the left flange 126 include a channel 180 disposed therein. The channel 180 is provided along the flanges 124, 126, 128 to receive an adhesive 182 that secures the substrate 30 to the frame 32 of the refill 22. The refill 22 may be comprised of greater or fewer numbers of flanges or support components that also may include the channel 180. A second channel (not shown) may be provided for structural or adhesive purposes. When the substrate 30 is secured to the frame 32, the substrate 30 is capable of carrying a volatile material 184 thereon and/or therein. In a preferred embodiment, the substrate 30 comprises a semi-permeable barrier defined by a plurality of connected strands. The connected strands are preferably flexible and crisscrossed to form a mesh web pattern and allow selective diffusion therethrough. In one embodiment, the substrate 30 comprises nylon.

The substrate 30 may include an integrated coupling mechanism for securement to the frame 32 or may be otherwise joined using adhesives, tape, staples, ultrasonic welding, hook and loop fasteners, and combinations thereof, or other means known in the art. In some embodiments, the substrate 30 is dosed with the volatile material 184 before use of the dispensing device 20. In other embodiments, the substrate 30 may be re-dosed after the volatile material 184 has vaporized. In a preferred embodiment, when all (or substantially all) of the indicator material 144 has volatized or evaporated from the use-up cue 34, this indicates to a user that the volatile material 184 has also completely, or substantially, volatized from the substrate 30. In one preferred embodiment, it is recognized that the indicator material 144 of the use-up cue 34 is completely (or substantially) volatilized when a coloration of the indicator material 144 is completely (or substantially) gone.

During use of the dispensing device 20, and after the substrate 30 is dosed with the volatile material 184, the volatile material will become entrained within the surrounding air to effect dispensing of the material. Active release rates of at least 0.05 milligrams per hour (mg./hr.) or higher are preferred. Suitable actives for the volatile material 184 are D-teflumethrin, metofluthrin, transfluthrin, prallethrin, vaporthrin, tefluthrin, and esbiothrin or other synthetic pyrethroids. In a preferred embodiment, metofluthrin and/or transfluthrin are used as the volatile material 184. In one embodiment, the amount of metofluthrin used is between about 40 mg and about 150 mg, or between about 60 mg and about 100 mg, or about 80 mg. In one embodiment, the amount of transfluthrin used is between about 200 mg and about 400 mg, or between about 250 mg and about 350 mg, or about 320 mg.

The volatile material 184 may solely comprise an active, or, for ease of handling, the volatile material 184 may further include an oil-based and/or water-based carrier, a hydrocarbon, an alcohol, for example, ethanol, or other solvent or carrier, and/or combinations thereof. In some embodiments, the volatile material 184 may include insect repellents, such as, for example, mosquito repellents. It is contemplated that one or more fragrances may be used as "use-up indicators," such that when a user can no longer perceive the scent of the fragrance(s), the strength of the insect control active is no longer effective for its intended purpose, and a new refill is required or the dispensing device 20 must be "recharged" with another dose of the composition. The "use-up indicators" may be included within the indicator material 144 and/or the volatile material 184. In some embodiments, the emanation rates of the fragrance(s) and that of the volatile material 184 and/or the indicator material 144 are substantially the same. In other embodiments, only the volatile material 184 and indicator material 144 are keyed to one another, as previously noted above, to indicate that the refill 22 should be replaced. Additional use-up cues may include individual or combinations of appearing and disappearing inks and the like. Any fragrance may be used herein and it is further contemplated that a fragrance may serve as a carrier.

The substrate 30 is preferably capable of holding a dose of the volatile material 184 in a relatively even distribution thereon and/or therein and also capable of allowing increased evaporation in response to air flow. For an active ingredient that is hydrophobic and migrateable at common environmental temperatures between about 10° C. and 40° C. (e.g., D-teflumethrin), a suitable substrate material includes, by way of example, nylon. The nylon may be characterized as having a basis weight ranging from 30 grams per square meter (gsm) to 150 grams per square meter (gsm) and may be fabricated from synthetic, natural, or combined synthetic and natural polymeric materials. In one preferred embodiment, the nylon is characterized by a thickness of between about 0.1 mm to about 0.8 mm, more preferably between about 0.2 mm to about 0.5 mm, and most preferably about 0.35 mm. The nylon is further characterized by a melting point of between about 150° C. to about 275° C., or between about 200° C. to about 250° C., or about 215° C. to about 225° C. The nylon has a mesh size of between about 5 strands per cm to about 80 strands per cm, between about 10 strands per cm to about 40 strands per cm, or most preferably about 16 strands per cm. In one embodiment, the nylon has a mesh size of between about 15 strands per cm to about 79 strands per cm.

Alternatively, the substrate 30 may entirely comprise a volatile active-permeable material or a porous material, such as a cellulose fiber-containing substrate. Cellulose fiber-based substrates may include an amount of cellulose by weight ranging from about 50% to about 99%, or about 75% to about 99%, or about 95% to about 99%, or about 97.5% to about 98.5%, or more or less. Similarly, cellulose fiber-based substrates may include an amount of a secondary material by weight ranging from about 1% to about 50%, or about 1% to about 25%, or about 1% to about 5%, or about 1.5% to about 2.5%, or more or less. Secondary materials may include, for example, binders, pigments, polymers, resins, dyes, combinations thereof, and other materials known in the art. In one embodiment, a cellulose fiber-based substrate may have about 98.5% cellulose and about 1.5% wet strength polyamide resin.

In one embodiment the substrate 30 may be formed from crepe paper, printer paper, A4 paper, and other cellulosic materials. Additional examples of materials contemplated for the substrate 30 may include plastics, polymers, fabrics, non-woven substrates, such as a PET non-woven substrate, and/or combinations thereof. Additionally, the substrate 30 may include combinations of manufactured, natural, and recycled or reclaimed materials. It is further contemplated that the substrate 30 may include a laminate composed of two or more layers of materials, wherein the laminate may include only volatile active-permeable materials or combinations of volatile active-permeable and impermeable materials, such as a metal or plastic layer. In some embodiments, the substrate 30 may be a first substrate and the refill 22 may further include a second substrate. In some embodiments, the first substrate may be made of or incorporate one material and the second substrate may be made of or incorporate a different material, such that the first and second substrates are partially or entirely made of different materials. In other embodiments, more substrate layers may be included. For example, the substrate 30 may be comprised of three, four, five, six, or more substrate layers.

Further criteria that may be relevant for choosing a substrate material include the thickness or caliper of the substrate 30. For example, the substrate 30 may have a thickness (±10%) of about 0.15 millimeters (mm), or about 0.3 mm, or about 0.4 mm, or about 0.5 mm, or about 1 mm, or about 2 mm, or about 3 mm, or about 5 mm, or about 10 mm. In addition, the basis weight of cellulosic materials may be of interest when choosing such substrates. For example, a basis weight (±10%) of about 250 grams per square meter (gsm), or about 300 gsm, or about 330 gsm may be desirable. Further, the rapidity of a cellulosic substrate may be considered. For example, a rapidity (±10%) ranging from about 30 to 50 milliliters per minute (ml/minute), or about 40 to 60 ml/minute, or about 50 to 70 ml/minute, or about 70 to 100 ml/minute, or a rapidity of about 50 ml/minute, or about 60 ml/minute, or about 70 ml/minute, or about 100 ml/minute may be desirable. Another factor to be considered for cellulosic substrates includes wet burst strength. For example, a desirable substrate may have a wet burst (±10%) of about 180 centimeters $H_2O$, or about 215 centimeters $H_2O$, or about 250 centimeters $H_2O$, or about 280 centimeters $H_2O$.

Rigidity or stiffness of the substrate 30 may be a further criterion for consideration in choosing the material that forms the substrate 30. Appropriate rigidity may aid in the appearance and stability of the refill 22 by reducing the amount of curl of the substrate 30 when impregnated with a composition and/or when exposed to humid conditions. Similarly, in one embodiment, it is preferable to use a substrate material with sufficient rigidity such that the substrate 30 substantially maintain its form or shape when the refill 22 is assembled within the device 20 and/or in use as previously discussed. In some embodiments, a bend is provided in one or more of the flanges 124, 126, 128 to maintain the rigidity of the refill 22. In embodiments where the region of rigidity 134 is included, a bend may be applied to the region of rigidity 134 to maintain the rigidity of the refill 22.

As shown in FIGS. 18-23, the refill 22 is slidingly coupled with the drive arm 24. The drive arm 24 includes an upper arm 220 and a lower arm 222. The upper arm 220 is positioned above the fulcrum or pivot 36 and the lower arm 222 is disposed below the pivot 36. The pivot 36 may comprise a rod 224 that is secured by one or more of the first portion 38 or the second portion 40 of the base 26. In a preferred embodiment, pivot holes 226 (see FIG. 8) are formed within the top wall 48 of the base 26 when the first portion 38 and the second portion 40 are coupled together and the rod 224 is positioned within the pivot holes. The drive arm 24 is therefore capable of pivoting about the rod 224 when the rod is secured within the pivot holes 226.

Referring to FIGS. 18-21, the upper arm 220 includes a top rail 230, a bottom rail 232, and a support rail 234. The top and bottom rails 230, 232 engage with a front side 236 of the support base 120 of the refill 22 while the support rail 234 engages with a rear side 238 of the support base 120. The rails 230, 232, 234 act as a track 240 within which the refill 22 can slide to be secured to the drive arm 24 before use of the dispensing device 20. In a preferred embodiment, a bottom face of the top rail 230 and an upper face of the bottom rail 232 interface with the horseshoe shaped support indentations 174 of the support base 120. When the refill 22 is engaged within the drive arm 24, the protrusion 172 is centrally disposed along the support rail 234 and engages with the groove 170 of the support base 120. In other embodiments, the support base 120 may include other grooves or support indentations that act as retention mechanisms and allow the refill 22 to interface with, and be supported by, the drive arm 24.

As illustrated in FIGS. 18-22 the upper arm 220 of the drive arm 24 also includes a lateral stop 250 that extends outwardly from an intersection of the rails 230, 232, 234. The lateral stop 250 operates as a mechanism to prevent the substrate 30 from touching the first and second shades 50, 52, when the dispensing device 20 is in use. Specifically, in the present embodiment the lateral stop 250 would impinge upon side edges of the first and/or second shades 50, 52 during the pendulum-like movement of the drive arm 24 to prevent over rotation in a manner that would allow the substrate 30 to impinge on inner surfaces of the first and second shrouds 50, 52. In one embodiment, the lateral stop 250 has an aperture 252 for purposes of ease of manufacturing and/or user interface considerations.

Figure 18:
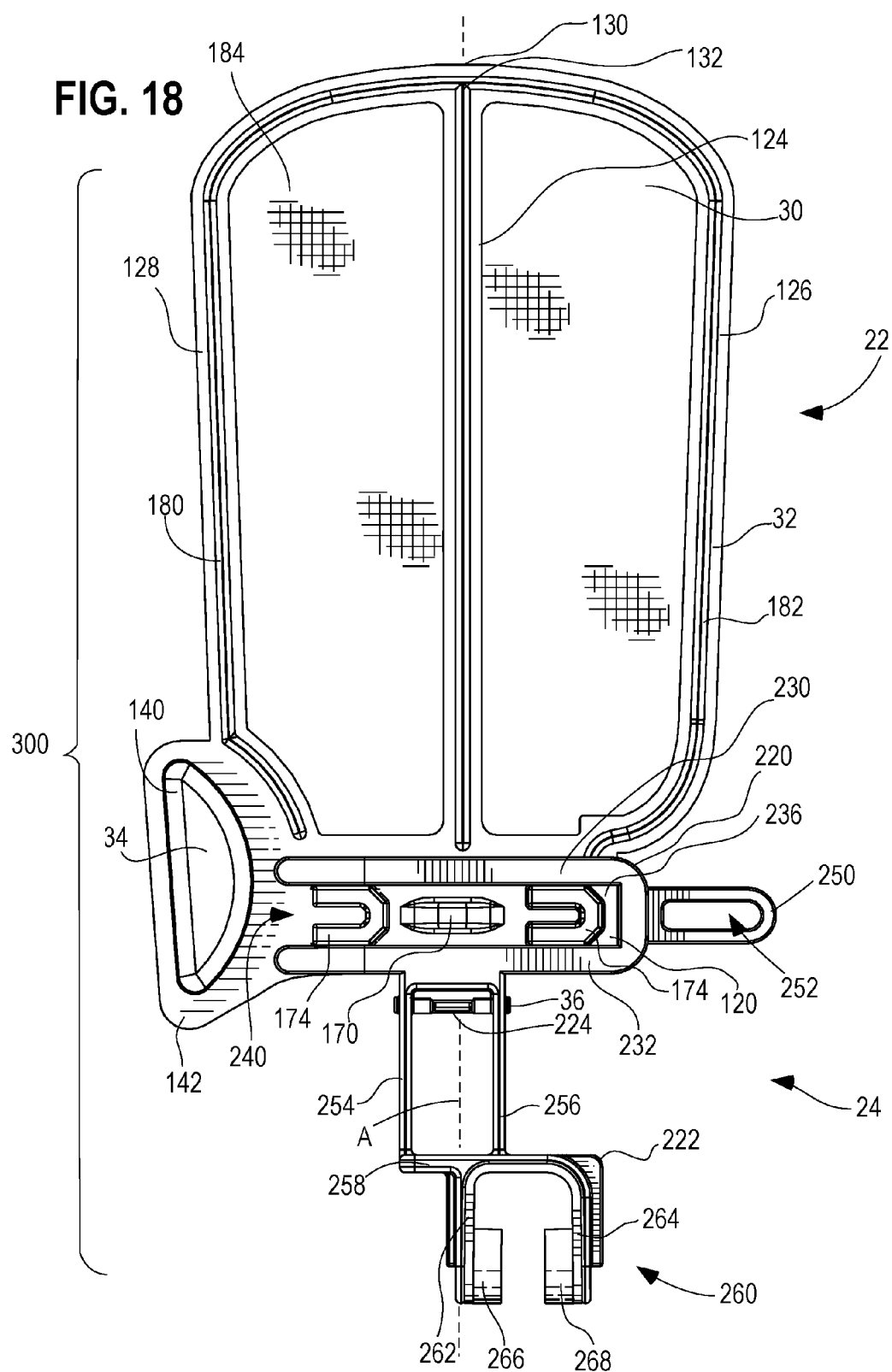
FIG. 18 is a front elevational view of the refill of FIG. 9 slidingly coupled with a drive arm.
Figure 19:
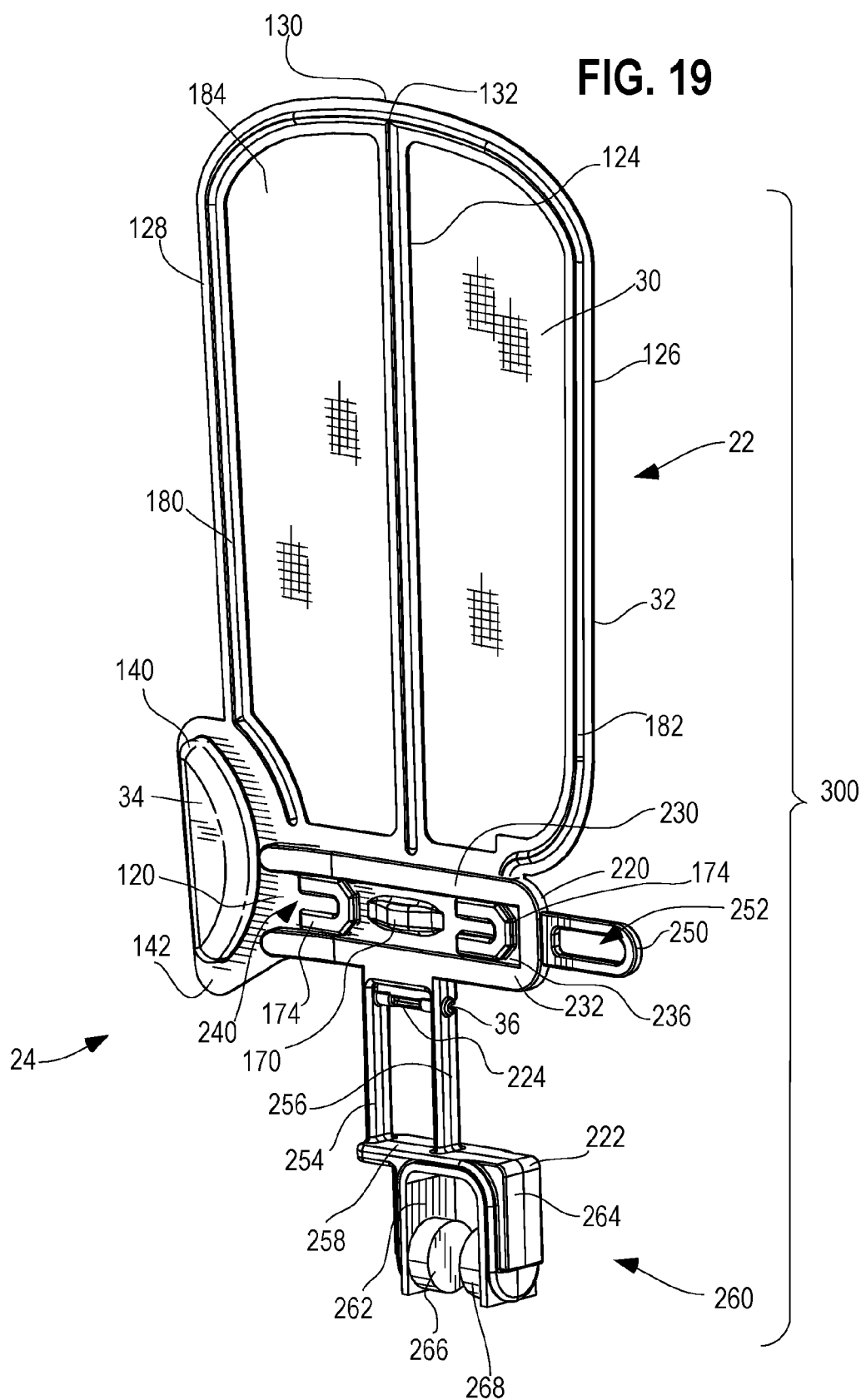
FIG. 19 is a front isometric view of the refill and drive arm of FIG. 18.

With specific reference to FIGS. 18 and 19, the upper arm 220 of the drive arm 24 is connected to the lower arm 222 at the pivot 36. The lower arm 222 includes a right vertical bar 254 and a left vertical bar 256. The pivot rod 224 is connected to both the right vertical bar 254 and the left vertical bar 256 where the upper arm 220 of the drive arm 24 meets the lower arm 222 of the drive arm 24. The rod 224 further engages with the top wall 48 of the base 26 as described above. The right vertical bar 254 and the left vertical bar 256 are further coupled with an upper ledge 258 of a magnet frame 260. The magnet frame 260 includes the upper ledge 258, a right leg 262, and a left leg 264. The right leg 262 and the left leg 264 depend downward from the upper ledge 258 of the magnet frame 260. A first magnet 266 is coupled with the right leg 262 and a second magnet 268 is coupled with the left leg 264. In a preferred embodiment, the first and second magnets 266, 268 are permanent magnets and may be formed of iron, iron alloys, nickel, nickel alloys, cobalt, cobalt alloys, rare earth metal alloys, or any other material known to those of ordinary skill in the art. As illustrated in FIG. 18, the magnet frame 260 is offset from a central axis A of the substrate. In other embodiments, the magnet frame 260 may be centered or may be positioned in a different location. In some embodiments, the location of the magnet frame 260 is dependent upon the configuration of components of the dispensing device 20 positioned within the base 26. For example, in some embodiments, the magnet frame 260 is offset to minimize space within the base 26 and/or to allow for incorporation of the electrical components of the device 20.

In some embodiments, the upper arm 220, inclusive of the rails 230, 232, 234 and the lateral stop 250, and the lower arm 222, inclusive of the vertical bars 254, 256 and the magnet frame 260, are integrally formed. In other embodiments, one or more of the aforementioned components may be separately formed and coupled to one another. Additionally, the components may be made from the same or different materials.

Figure 22:
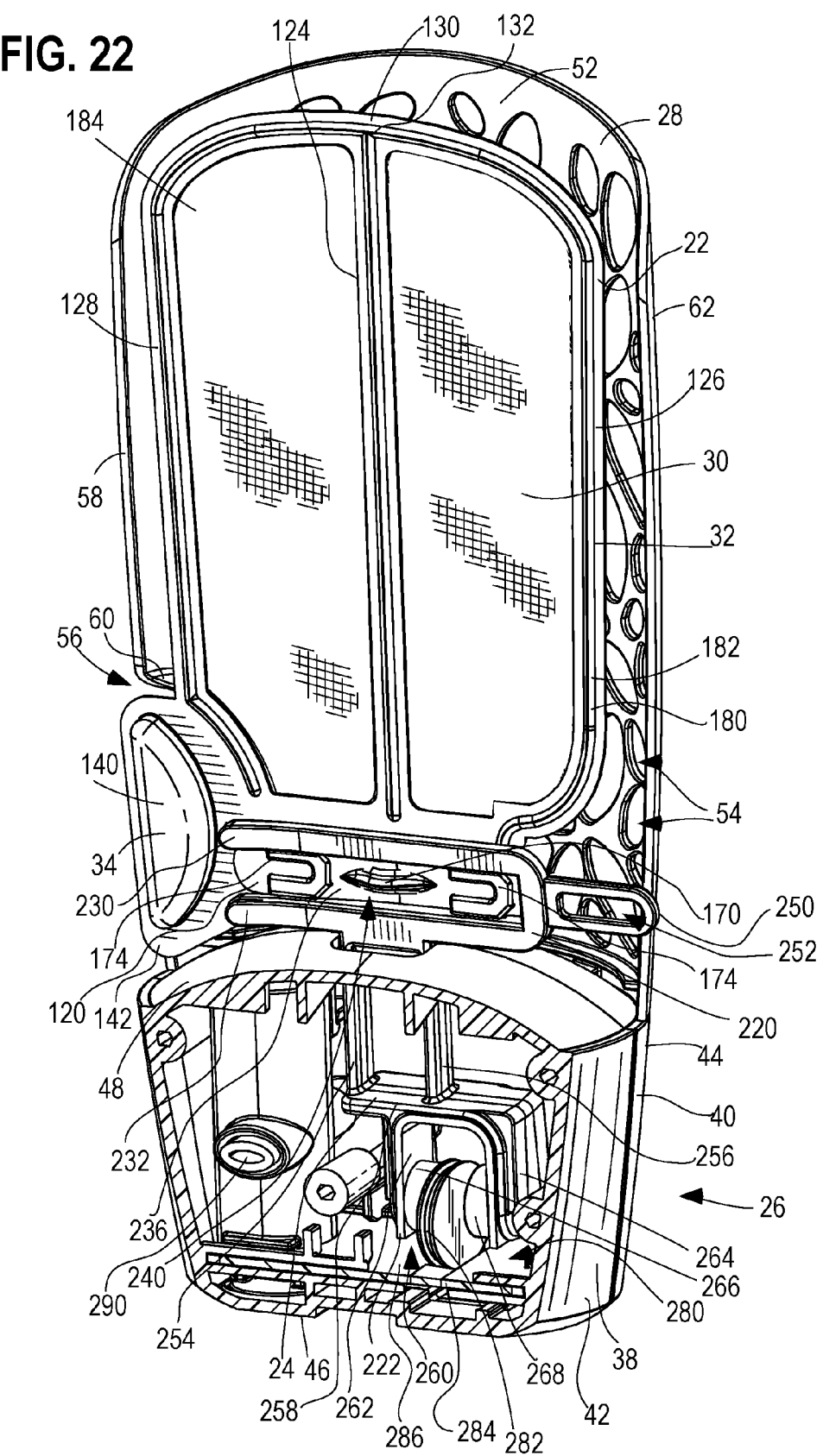
FIG. 22 is a front isometric, cross sectional view of the device taken along line 22-22 of FIG. 1 with a front shade attachment removed.
Figure 23:
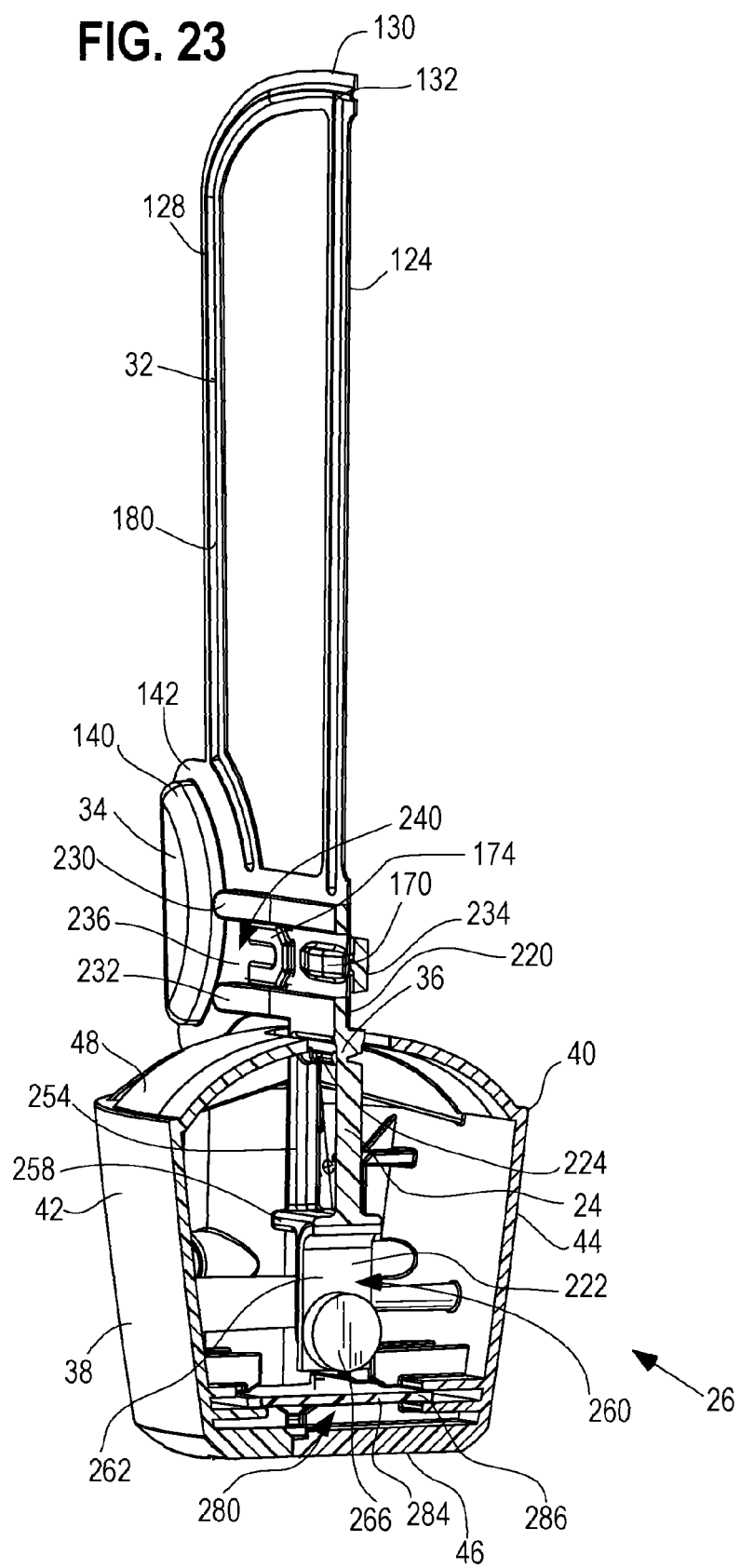
FIG. 23 is a front isometric, cross sectional view of the device taken along line 23-23 of FIG. 1 with a substrate, a front shade attachment, and a rear shade attachment removed.

Referring to FIGS. 22 and 23, the base 26 is generally hollow and contains a drive mechanism 280. The drive mechanism comprises a drive magnet 282, which may include one or more coils of wire, and an electronics unit 284, which may include a printed circuit board (PCB) having one or more capacitors, resistors, transistors, logic circuits, or other electronic components disposed thereon. It is also contemplated that the electronics unit 284 may comprise a microcontroller, a processor, or a memory. In a preferred embodiment, the drive magnet 282 is an electromagnet that is mounted beneath a drive magnet mount plate 286. In a preferred embodiment, the drive magnet 282 comprises one or more coils wound with wire. In some embodiments, the drive magnet 282 includes both a sensing coil and a firing coil. In a preferred embodiment, the sensing coil has between about 1000 turns and about 3000 turns of wire, or between about 1500 turns and about 2500 turns of wire, or about 2100 turns of wire. In a preferred embodiment, the firing coil has between about 1000 turns and about 3000 turns of wire, or between about 1500 turns and about 2500 turns of wire, or about 2100 turns of wire.

The magnet frame 260 of the drive arm 24 is positioned directly over the drive magnet 282. The first and second magnets 266, 268 are in close proximity to the drive magnet 282 such that there is a strong attractive or repulsive force between the magnets 266, 268 and the drive magnet 282. The number and/or type of magnets on the drive arm 24 may modified to increase or decrease the magnetic force between the magnets 266, 268 and the drive magnet 282. In a preferred embodiment, one or more of the magnets 266, 288 have a diameter of between about 5 mm and about 20 mm, or between about 10 mm and about 17 mm, or about 14.5 mm. In a preferred embodiment, one or more of the magnets comprises ferrite.

The drive magnet 282 is electrically connected to the electronics unit 284. The connection is made such that when the drive current is switched on, the drive magnet 282 electromagnetic field is of similar polarity to the adjacent fixed magnetic field of the first and second magnets 266, 268, and as a result, the magnets 266, 268 are repelled. Referring to FIG. 7, the current is switched on when a user moves the switch 76 from an "off" position to one or more "on" positions. The "on" position(s) may include differing levels of power, and therefore may affect the speed with which the refill 22 oscillates back and forth within the device 20. In a preferred embodiment, the "on" positions include a "low" setting and a "high" setting. The switch 76 is electrically coupled with an energy source 290 and the drive magnet 282. In a preferred embodiment, the energy source 290 is a double A battery. In other embodiments, the energy source 290 may be a triple A battery, a 9V battery, or any other battery known to those skilled in the art. The energy source 290 further may be a solar panel, a wind turbine, or any other renewable energy source known to those of ordinary skill in the art.

Referring to FIGS. 18 and 19, the combination of the refill 22 and the drive arm 24 is hereinafter referred to as a pendulum 300. When not in use, i.e. when the switch 76 is in the "off" position, a centering force caused by attraction between the magnets 266, 268 and the drive magnet 282 keeps the drive arm 24 centered. Thus, the electromagnet drive current may then be switched on and off, resulting in an alternating attraction (off), then repulsion (on) force between the drive magnet 282 and the permanent magnets 266, 268. This alternating attraction and repulsion effect forms the basis of the drive system for the pendulum 300.

It is further contemplated that the period of the applied drive may be fixed or variable. The duty-cycle of the pulses may be varied or fixed, and the current pulses of the drive magnet 282 may be linear (periodic or regular) or non-linear (aperiodic or interrupted). Adjustment of the aforementioned parameters can influence the overall operation of the pendulum 300. If the frequency of the applied current cycle of the drive magnet 282 is adjusted to approximately twice the natural period of the pendulum 300, and the travel of the pendulum 300 is unhindered, the pendulum 300 will settle quickly into classical regular motion, not unlike that of a clock. In some embodiments, the pendulum 300 is a chaotic pendulum, which, due to its design, typically cannot be made to operate in a linear fashion for extended periods.

While a preferred embodiment of the pendulum 300 described herein operates through the use of a combination of permanent and electromagnets, other drive mechanisms are contemplated. For example, a spring system may be implemented to oscillate or undulate the refill 22 back and forth. In another embodiment, a motor may be used to oscillate the refill 22. In still a further embodiment, a different configuration of magnets may be used to oscillate the refill 22. Any electromechanical or mechanical means for oscillating or manipulating the refill 22 may be provided within the base 26 to enable the refill 22 to sway or undulate.

Now that the individual components and the assembly of the dispensing device 20 have been discussed, the relationship thereto and the operation of the dispensing device will be discussed. Prior to use, the dispensing device 20 is preferably provided to a user in a sealed container (not shown), such as a bag, box, or other package. When a user desires to use the dispensing device 20, the user opens the container and removes the dispensing device 20 therefrom. In some embodiments, the user is required to attach the shade 28 to the base 26; however, it is also contemplated that the shade 28 comes preassembled to the base 26.

Next, the user removes any packaging from around the substrate 30 and/or the refill 22. Thereafter, the user removes the peel-off cover 152 from the use-up cue 34 and any frangible portion (for example, frangible portion 146) if one is provided. The refill 22 is now in an operational state and ready for insertion into the dispensing device 20. In such an operational state, the volatile material 184 and the indicator material 144 may passively diffuse into the ambient air. A user may now slidingly insert the refill 22 into the upper arm 220 of the drive arm 24 such that the indentations 174 and groove 170 of the refill 22 engage with the rails 230, 232, 234 and the protrusion 172, respectively, of the drive arm 24. The dispensing device 20 may now be characterized as being in an operable state. In such an operable state, the user can now manipulate the switch 76 from the off position (inactive state) to one or more of the on positions (active state). As a result, the refill 22 begins to oscillate or undulate during this active state. Since the position drive magnet 282 is fixed, and the magnets 266, 268 are free to move, motion occurs between the two bodies. The initial direction of the resultant motion is determined by whatever slight variances may exist in the initial positions of the magnets 266, 268.

Once the user has turned the switch 76 to one of the "on" positions, the dispensing device 20 is capable of operating on its own. In a preferred embodiment, the energy source 290 provides energy for the device 20 to function for about six months, or about 180 days. In some embodiments, the energy source 290 provides energy for the device 20 to function for between about 40 days and about 280 days, or between about 80 days and about 240 days, or between about 120 days and about 200 days. Also in a preferred embodiment, the use-up cue 34 contains between about 0.5 g and about 5 g of indicator material, or about 1 g of indicator material. As a result, the refill 22 can be used for about six months, or about 180 days. In some embodiments, the refill 22 can be used for between about 3 days and about 60 days, or between about 7 days and about 30 days, or between about 10 days and about 20 days, or about 14 days.

During the active state, the dispensing device 20 is preferably positioned on a flat surface and away from other objects to enhance the air flow therearound. In such an active state, the dispensing device 20 preferably has a release rate of the volatile material 184 of between about 0.01 to about 0.1 mg/hour, as measured at about 25° C. and an air flow of between about 0.01 to about 0.2 m/s. Although designed to be used with airflow, the dispensing device 20 will still release at least some of the volatile material 184 with little or no airflow. In one particular embodiment, during the inactive state, i.e. when the dispensing device 20 is in an "off" position, the dispensing device 20 has a release rate of between about 0.005 to about 0.08 mg/hr, at about 25° C. and an air flow of between about 0.01 to about 0.2 m/s. In other embodiments, during the inactive state, the dispensing device 20 has a release rate of between about 0.02 to about 0.4 mg/hr, at about 25° C.

Figure 24:
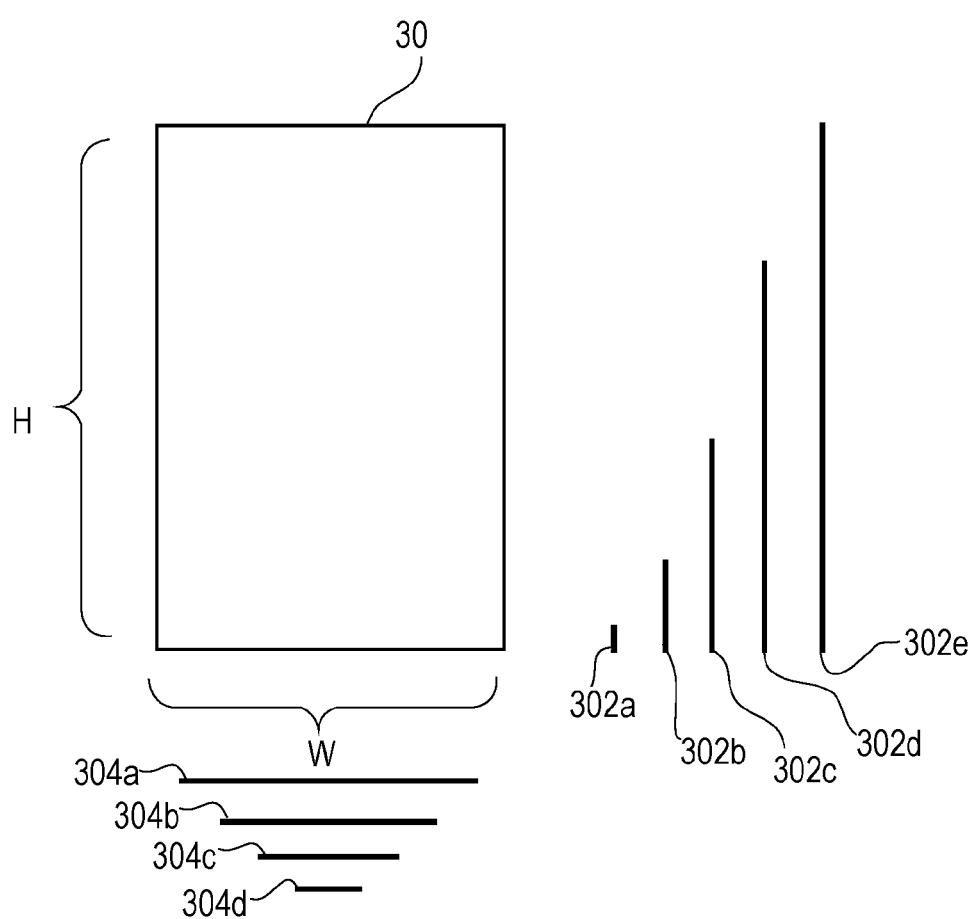
FIG. 24 is a schematic representation of a refill that illustrates the varying heights and widths of flanges and support bases comprising the refill frame.

Referring to FIG. 24, a schematic illustration of the substrate 30 is depicted that shows varying heights, H, and widths, W, that one or more flanges 302 and one or more support bases 304 may have when constructed to form the frame 32. The heights and widths are relative and compared to a largest height, H, and a largest width, W, of the substrate 30. For example, in one embodiment, a flange 302a may have a height of between about 1/20H and about 1/10H. In another embodiment, a flange 302b may have a height of between about 1/10H and about 3/10H. Still further, a flange 302c may have a height of between about 3/10H and about 7/10H. In some embodiments, a flange 302d may have a height of between about 7/10H and about 9/10H. Still further, a flange 302e may have a height of about H. In some embodiments, flanges 302 of varying heights are used to construct the frame 32.

Still referring to FIG. 24, in one embodiment, a support base 304a may have a width of between about 4/5 W and about W. In some embodiments, a support base 304b may have a width of between about 2/5 W and about 4/5 W. In other embodiments, a support base 304c may have a width of between about 1/5 W and about 2/5 W. In some embodiments, a support base 304d may have a width of less than 1/5 W. The frame 32 may not include a support base 304, or may include more than one support base 304.

Referring to FIG. 25, the refill 22 of FIG. 9 includes an attachment mechanism 400 provided thereon. In the illustrated embodiment, the attachment mechanism 400 is a string that is looped through a hole 402 within the base 120 of the refill 22. The attachment mechanism 400 is a closed loop of string that can be hung from a hanging element (not shown). In the illustrated embodiment, the hole 402 is positioned directly below the groove 170. However, in other embodiments, the hole 402 may be positioned along any portion of the base 120, the flanges, 124, 126, 128, or the substrate 30.

In other embodiments, the string may be a single open ended strand of string, as opposed to a closed loop. In still other embodiments, the attachment mechanism 400 comprises one or more flexible and/or elongate materials, which may include string, twine, cord, yarn, thread, rope, wire, chains, or any other material. In different embodiments, the attachment mechanism 400 may alternatively comprise a clip, an adhesive, a hook, a clasp, a nail, a screw, or any other means for attaching known to those of ordinary skill in the art.

Referring to FIG. 26, the refill 22 may comprise the support base 120, one or more of the flanges 124, 126, 128, and the substrate 30, without inclusion of the use-up cue 34 or other retention mechanisms previously noted above. The refill 22 may further include the attachment mechanism 400 looped through the hole 402 in any form as described in connection with the embodiment of FIG. 25 above.

Any of the embodiments described herein may be modified to include any of the structures or methodologies disclosed in connection with different embodiments. Further, the present disclosure is not limited to substrate and/or support component shapes/sizes of the type specifically shown. Still further, the support components of any of the embodiments disclosed herein may be modified to work with various types of substrates consistent with the disclosure herein.

INDUSTRIAL APPLICABILITY

Numerous modifications to the present disclosure will be apparent to those skilled in the art in view of the foregoing description. Accordingly, this description is to be construed as illustrative only and is presented for the purpose of enabling those skilled in the art to make and use the device disclosed herein and to teach the best mode of carrying out same. The exclusive rights to all modifications which come within the scope of the appended claims are reserved.

We claim:

1. A dispensing device for release of a volatile material, comprising:
    a base;
    a drive arm coupled to a pendulum based drive mechanism; and
    a refill coupled to the drive arm,
        wherein the refill includes:
            a support base and at least one flange,
            a substrate coupled with the at least one flange, and
            a use-up cue.

2. The dispensing device of claim 1 further including one or more magnets disposed along a lower arm of the drive arm.

3. The dispensing device of claim 1 further including a left flange and a right flange that extend from the support base, and
    wherein the refill further includes a volatile material disposed on the substrate.

4. The dispensing device of claim 3 further including a center flange that extends from the support base.

5. The dispensing device of claim 1 further including one or more shade attachments coupled with the base.

6. The dispensing device of claim 5, wherein the one or more shade attachments each include a plurality of flow apertures.

7. The dispensing device of claim 5, wherein the one or more shade attachments are non-removably inserted into the base.

8. A refill for dispensing a volatile material, comprising:
    a support base;
    one or more flanges extending from the support base;
    one or more retention mechanisms disposed on the support base;
    a substrate coupled with the one or more flanges; and
    a use-up cue.

9. The refill of claim 8, wherein the use-up cue includes a semi-permeable membrane and a removable impermeable membrane is provided over the semi-permeable membrane.

10. The refill of claim 9 further including a frangible portion adjacent the use-up cue.

11. The refill of claim 9, wherein the use-up cue includes a reservoir holding an indicator material, which diffuses through the semi-permeable membrane when the removable impermeable membrane is removed therefrom.

12. The refill of claim 8 further including a volatile material disposed on the substrate, and wherein the substrate comprises a non-woven material.

13. The refill of claim 12, wherein the volatile material is one of metofluthrin or transfluthrin, and wherein the substrate comprises nylon.

14. A refill for dispensing a volatile material, comprising:
    a support base;
    at least one retention mechanism provided on the support base;
    a substrate coupled with the support base, wherein a volatile material is provided on the substrate; and
    one or more flanges provided along the substrate.

15. The refill of claim 14, wherein the at least one retention mechanism includes a first indentation, a second indentation, and a groove.

16. The refill of claim 15, wherein the first indentation and the second indentation extend outward from a front face of the support base.

17. The refill of claim 16, wherein the groove extends outward from a back face of the support base.

18. The refill of claim 16, wherein the first and second indentations are U shaped.

19. The refill of claim 14, wherein the one or more flanges extend from the support base.

20. The refill of claim 19 further including a left flange, a right flange, and a center flange.

* * * * *